US012376971B2

(12) United States Patent
Babaris et al.

(10) Patent No.: US 12,376,971 B2
(45) Date of Patent: Aug. 5, 2025

(54) BONE MILL WITH AN ACCESSIBLE MILLING ELEMENT

(71) Applicant: Stryker Corporation, Kalamazoo, MI (US)

(72) Inventors: Robin B. W. Babaris, Portage, MI (US); Aaron Hoffmann, Plainwell, MI (US); Clifford Edwin Lambarth, Portage, MI (US); Derek F. Nelson, Kalamazoo, MI (US); Steven M. Rolfsen, Jr., Kalamazoo, MI (US); Shammodip Roy, Wayne, NJ (US); James Walen, Portage, MI (US); Jason James Wroblewski, Portage, MI (US)

(73) Assignee: Stryker Corporation, Portage, MI (US)

( * ) Notice: Subject to any disclaimer, the term of this patent is extended or adjusted under 35 U.S.C. 154(b) by 168 days.

(21) Appl. No.: 18/147,840

(22) Filed: Dec. 29, 2022

(65) Prior Publication Data
US 2023/0135274 A1 May 4, 2023

Related U.S. Application Data

(63) Continuation of application No. 16/616,866, filed as application No. PCT/US2018/034700 on May 25, 2018, now Pat. No. 11,564,813.
(Continued)

(51) Int. Cl.
*A61F 2/46* (2006.01)
*A61B 17/16* (2006.01)
(Continued)

(52) U.S. Cl.
CPC ........ *A61F 2/4644* (2013.01); *A61B 17/1635* (2013.01); *A61B 2017/00123* (2013.01);
(Continued)

(58) Field of Classification Search
CPC ...................... A47J 43/0772; A61F 2002/4645
See application file for complete search history.

(56) References Cited

U.S. PATENT DOCUMENTS 3,612,414 A    10/1971  Nevison et al.
3,892,365 A *   7/1975  Verdun .................. A47J 43/06
                                              241/37.5
(Continued)

FOREIGN PATENT DOCUMENTS

AU    2014227548 A1    11/2014
CN      101420915 A     4/2009
(Continued)

OTHER PUBLICATIONS

English language abstract for CN 104161607 A extracted from espacenet.com database on Jul. 22, 2021, 2 pages.
(Continued)

*Primary Examiner* — David W Bates
(74) *Attorney, Agent, or Firm* — Howard & Howard Attorneys PLLC

(57) ABSTRACT

A milling module for converting bone stock into bone chips comprises a shell adapted for releasable attachment to a base module. The shell has an inlet opening through which bone stock is introduced into the shell and an outlet opening through which bone chips are discharged from the shell. A milling element is moveably disposed in the shell between the inlet opening and the outlet opening for converting bone stock into bone chips. The shell includes a base adapted for releasable attachment to the base module. The base includes the outlet opening and a lid removably attached thereto. The lid includes the inlet opening of the shell. The base and the lid are collectively configured so that removal of the lid from the base allows the milling element to be accessed.

15 Claims, 13 Drawing Sheets

Related U.S. Application Data

(60) Provisional application No. 62/511,590, filed on May 26, 2017.

(51) Int. Cl.
*A61B 17/00* (2006.01)
*A61B 90/00* (2016.01)

(52) U.S. Cl.
CPC .............. *A61B 2090/0808* (2016.02); *A61F 2002/4645* (2013.01)

(56) References Cited

U.S. PATENT DOCUMENTS

| | | | |
|---|---|---|---|
| 4,095,751 A * | 6/1978 | Artin | A47J 43/0772 241/37.5 |
| 4,371,118 A * | 2/1983 | Sontheimer | F16P 3/10 241/37.5 |
| 5,071,077 A * | 12/1991 | Arroubi | A47J 43/06 99/511 |
| 6,287,312 B1 | 9/2001 | Clokie et al. | |
| 6,755,365 B1 | 6/2004 | Meredith | |
| 6,824,087 B2 | 11/2004 | McPherson et al. | |
| 7,131,605 B2 | 11/2006 | McPherson et al. | |
| 7,588,202 B2 | 9/2009 | Rasekhi | |
| 7,927,336 B2 | 4/2011 | Rasmussen | |
| 8,512,342 B2 | 8/2013 | Meredith | |
| 8,622,953 B2 | 1/2014 | Hynes et al. | |
| 8,740,114 B2 | 6/2014 | Koltz et al. | |
| 9,622,865 B2 | 4/2017 | Vogt | |
| 10,258,201 B1 | 4/2019 | Rasekhi | |
| 10,258,484 B2 | 4/2019 | Pressacco et al. | |
| 2004/0155132 A1 | 8/2004 | McPherson et al. | |
| 2009/0118713 A1 | 5/2009 | Munson | |
| 2009/0118735 A1 * | 5/2009 | Burmeister, III | B02C 18/24 606/169 |
| 2009/0157082 A1 | 6/2009 | Meredith | |
| 2010/0004653 A1 | 1/2010 | Rasekhi | |
| 2012/0310243 A1 | 12/2012 | Stratton et al. | |
| 2014/0263778 A1 | 9/2014 | Koltz et al. | |
| 2014/0303623 A1 | 10/2014 | Diehl et al. | |
| 2014/0306047 A1 | 10/2014 | Lee et al. | |
| 2019/0029846 A1 | 1/2019 | Horton, IV et al. | |
| 2020/0100915 A1 | 4/2020 | Babaris et al. | |

FOREIGN PATENT DOCUMENTS

| | | |
|---|---|---|
| CN | 104161607 A | 11/2014 |
| CN | 105361982 A | 3/2016 |
| JP | 84935151 B1 | 9/1974 |
| WO | 2009061728 A1 | 5/2009 |
| WO | 2017019827 A2 | 2/2017 |

OTHER PUBLICATIONS

English language abstract not found for JPS 49-35151 B1; however, see English language equivalent U.S. Pat. No. 3,612,414. Original document extracted from Japanese Patent Office on Jun. 1, 2022, 5 pages.
International Search Report for Application No. PCT/US2018/034700 dated Oct. 30, 2018, 6 pages.
Partial International Search Report for Application No. PCT/US2018/034700 dated Aug. 27, 2018, 2 pages.
Stryker Neuro Spine Ent, "The Mill Brochure", 2011, 2 pages.
English language abstract for CN 101420915 A extracted from espacenet.com database on Mar. 21, 2025, 2 pages.
English language abstract for CN 105361982 A extracted from espacenet.com database on Mar. 21, 2025, 2 pages.

* cited by examiner

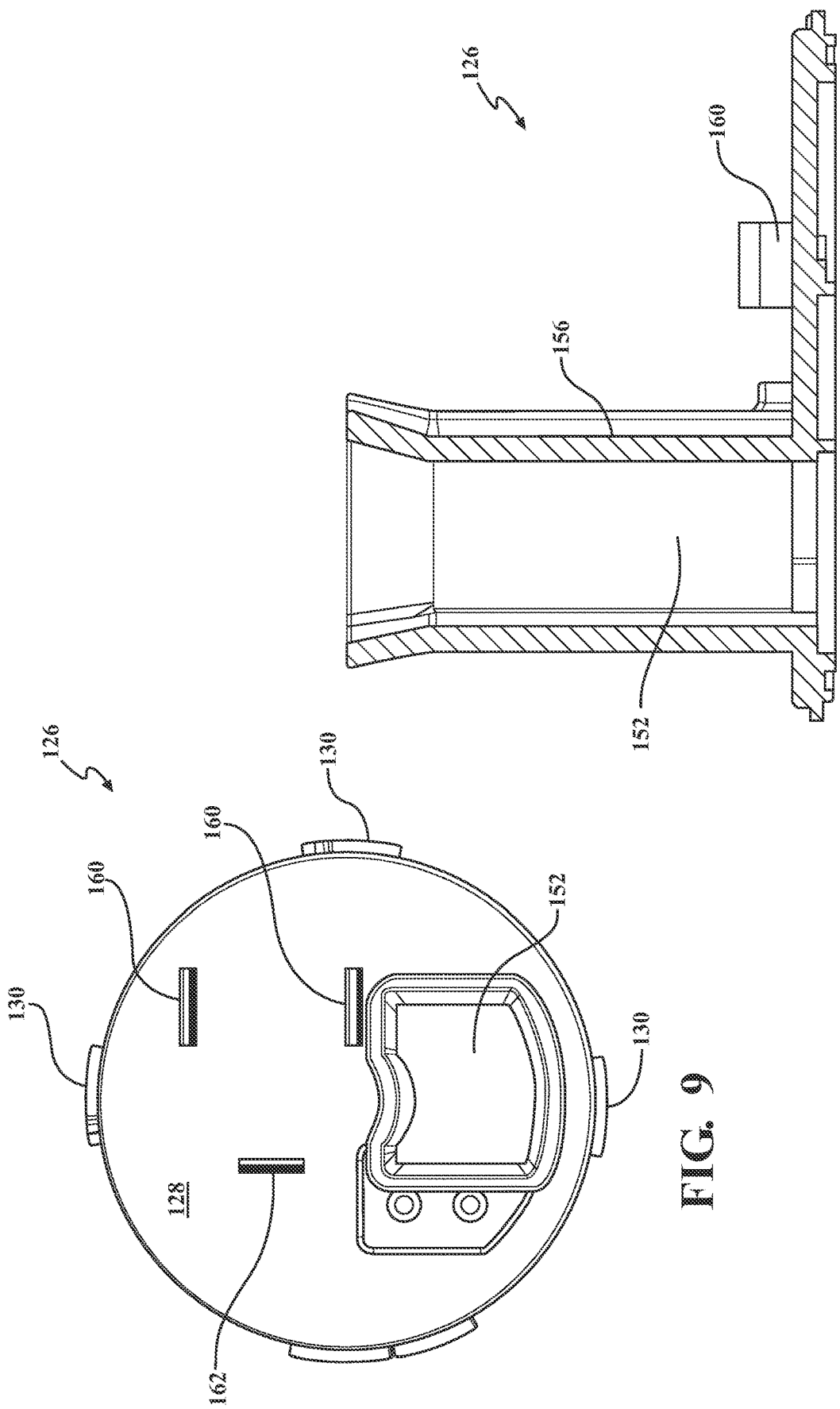

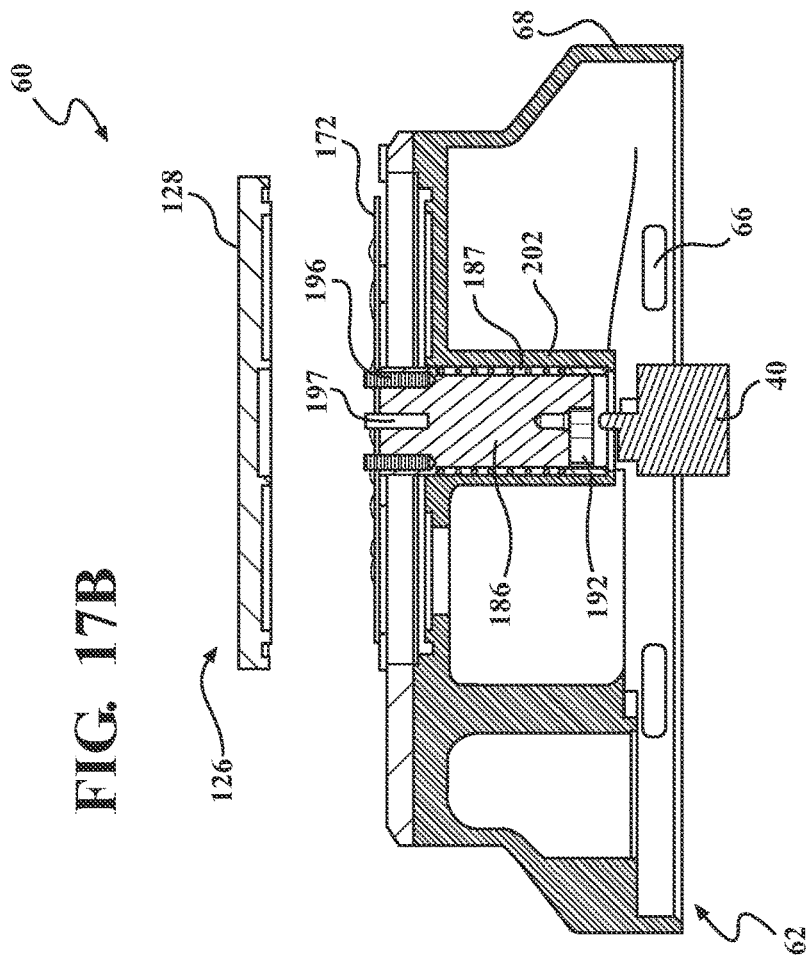
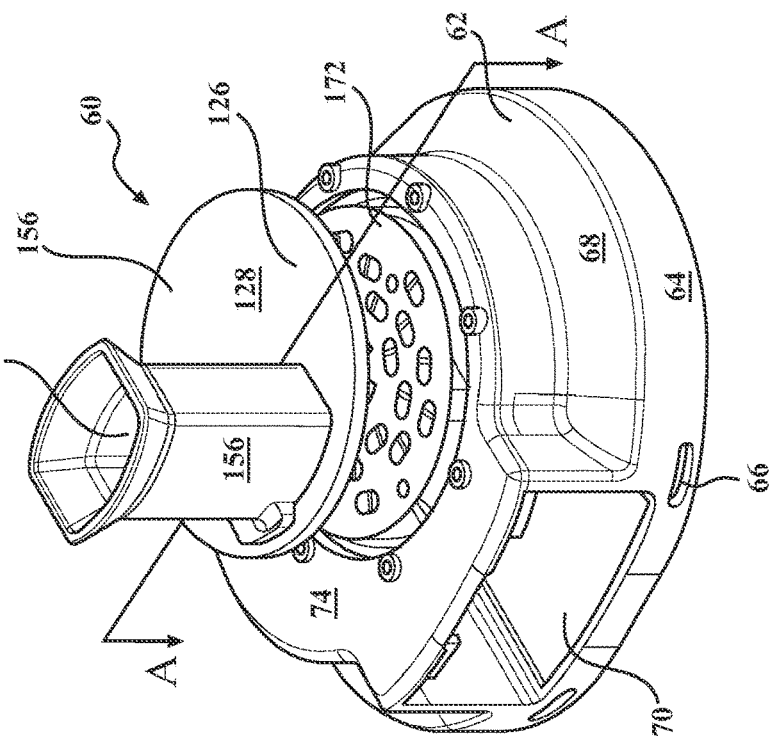
FIG. 17B
FIG. 17A

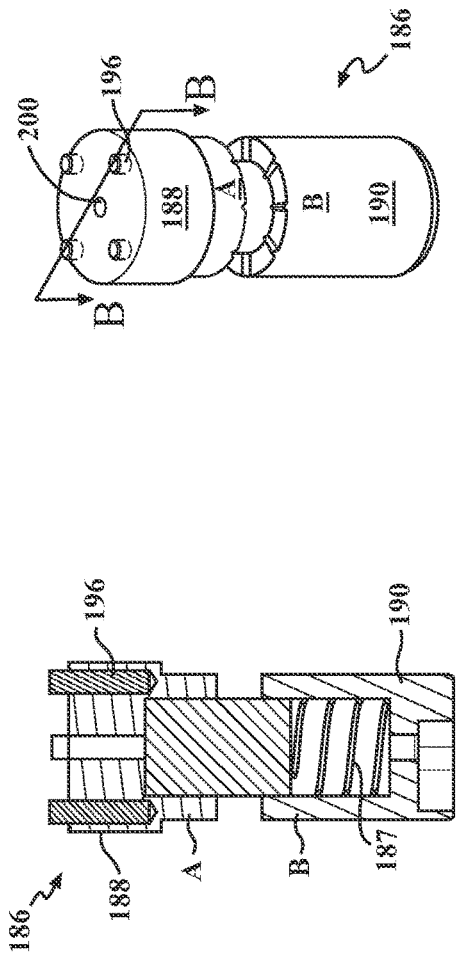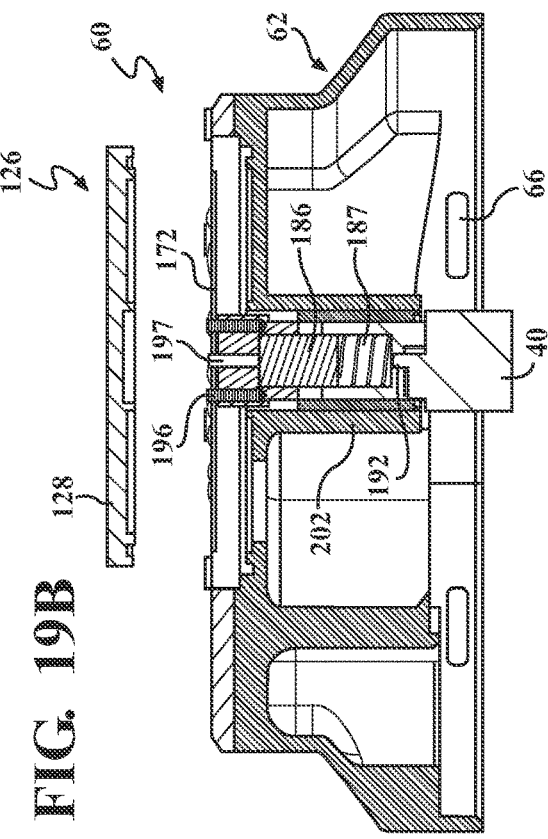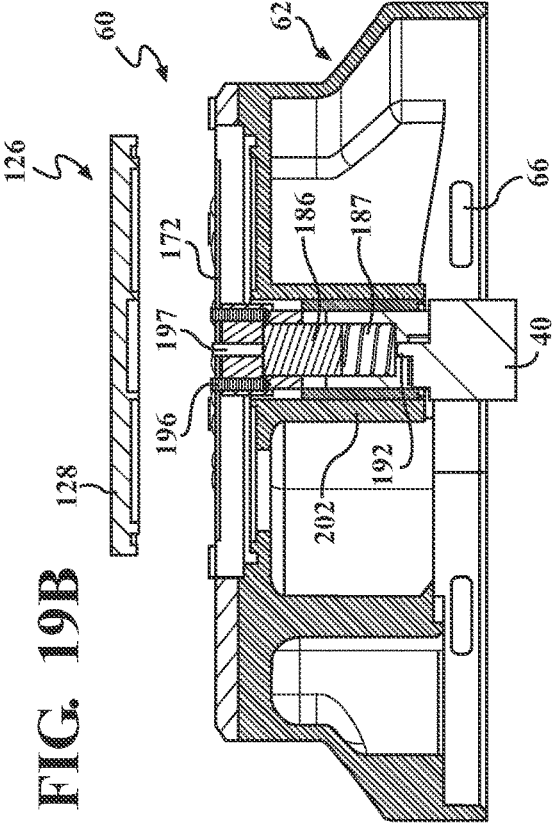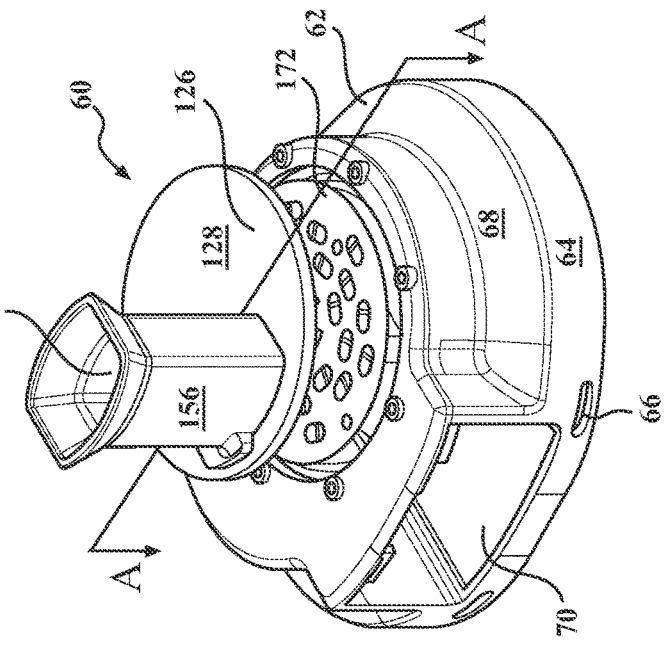

BONE MILL WITH AN ACCESSIBLE MILLING ELEMENT

CROSS-REFERENCE TO RELATED APPLICATIONS

This application is a continuation of U.S. patent application Ser. No. 16/616,866, filed on Nov. 25, 2019, which is the National Stage of International Patent Application No. PCT/US2018/034700, filed on May 25, 2018, which claims priority to and all the advantages of U.S. Provisional Patent Application No. 62/511,590, filed on May 26, 2017. The entire contents of these applications are incorporated herein by reference in their entirety.

FIELD OF THE DISCLOSURE

This disclosure relates generally to a bone mill used to form bone chips used in surgical procedures. More particularly, this disclosure is generally related to a bone mill that includes a milling element that can be accessed so as to remove bone chips adhering thereto.

BACKGROUND OF THE DISCLOSURE

In certain surgical procedures, chip-sized bone is used as filler adjacent intact bone. For example, in a spinal fusion procedure, it is known to place a compound that includes milled bone chips around implanted rods. The rods hold adjacent vertebrae in alignment. This compound serves as a lattice upon which tissues forming the vertebrae grow so as to form a foundation of bone around the rods. This foundation distributes the load imposed on the rods. Bone chips can also be placed in the intervertebral disc space or into a cage positioned in the intervertebral disc space.

Bone chips are also used as filler and/or a growth formation lattice in orthopedic surgical procedures and maxillofacial procedures. Bone chips are used as a filler and/or a growth formation lattice in these procedures because the proteins from which the bone is formed serve as make-up material from which the blast cells of the adjacent living bone cells form new bone.

The ideal source of bone stock for bone chips is the patient into whom the bone chips are to be packed. This is because the patient's own bone is less likely than donor bone to be rejected by the patient's immune system. Accordingly, in a procedure in which bone chips are required, bone stock is often harvested from one of the patient's bones that can afford to lose a small section of bone, typically between 0.25 and 3 cubic centimeters. Bone that is removed from the patient for transplant into another part of the patient is referred to as autograft bone.

Converting autograft bone stock into bone chips can be considered a two part process. In the first part of the process, the harvested bone is cleaned to remove the ligaments and other soft tissue that is not suitable for forming bone chips. The cleaned bone is then milled into bone chips. The Applicant's U.S. Patent Application Pub. No. US 2009/0118735 A1/PCT Pub. No. WO 2009/061728 A1, and U.S. Provisional Patent Application No. 62/197,780/PCT App. No. PCT/US2016/044386, the contents of each of which are hereby incorporated by reference, discloses an electrically operated bone mill capable of converting bone stock into bone chips. Generally, the bone mill of these documents includes a housing that has a top opening and first and second bottom openings. The first bottom opening is located below the top opening. The second bottom opening is located inward of the first bottom opening. A milling head, sometime called a cutting disc, is rotatably disposed in the housing between the top opening and the bottom openings. The housing is shaped to be releasably coupled to a base module. Internal to the base module is a motor. The motor rotates a spindle. When the mill is seated on the base module, the spindle engages the milling head through the second bottom opening. The rotation of the spindle thus results in a like rotation of the milling head. Attached to the housing so as to be located below the first bottom opening is a catch tray.

Bone chips are formed using the above-described mill by inserting bone stock in the top openings while simultaneously rotating the milling head. The milling head is designed to push the bone stock against a static impingement surface adjacent the top opening. The pressing of the bone stock against the impingement surface resulting in the shearing of the relatively large volume bone stock into plural smaller volume bone chips. Many of the bone chips pass through openings in the mill head so as to fall through the first bottom opening into the catch tray. At the conclusion of the milling process, the catch tray is removed from the housing. The bone chips held in the catch tray are the bone chips that surgeon has available for fill.

The above described mill is a useful device in a surgical procedure for converting bone stock into smaller in size bone chips.

When bone stock is harvested to convert the stock into bone chips, ideally no more bone stock is harvested than is needed to supply the necessary volume of bone chips. This is because the minimizing the volume of bone stock that is harvested from the patient results in a like minimization of the trauma to the bone from which the stock was harvested and the tissue that surrounds that bone.

BRIEF DESCRIPTION OF THE DRAWINGS

The disclosure is pointed out with particularity in the claims. The above and further features and benefits of this disclosure are understood from the following Detailed Description taken in conjunction with the accompanying drawings in which:

FIG. 9 is a top plane view of the lid;

FIG. 10 is a cross sectional view of the lid;

FIG. 17A is a perspective view of a milling module including a lid which is not attached to a foundation, and a cutting element which includes a cutting disc, a shaft, and a spring;

FIG. 17B is a cross sectional view along line A-A of the milling module of FIG. 17A;

FIG. 19A is a perspective view of a milling module including a lid which is not attached to a foundation, and a cutting element which includes a cutting disc, a shaft, and a spring;

FIG. 19B is a cross sectional view along line A-A of the milling module of FIG. 19A;

FIG. 19C is an enlarged perspective view of the shaft and the spring of FIGS. 19A and 19B; and FIG. 19D is a cross sectional view along line B-B of the shaft and the spring of FIG. 19C.

DETAILED DESCRIPTION

Figure 1:
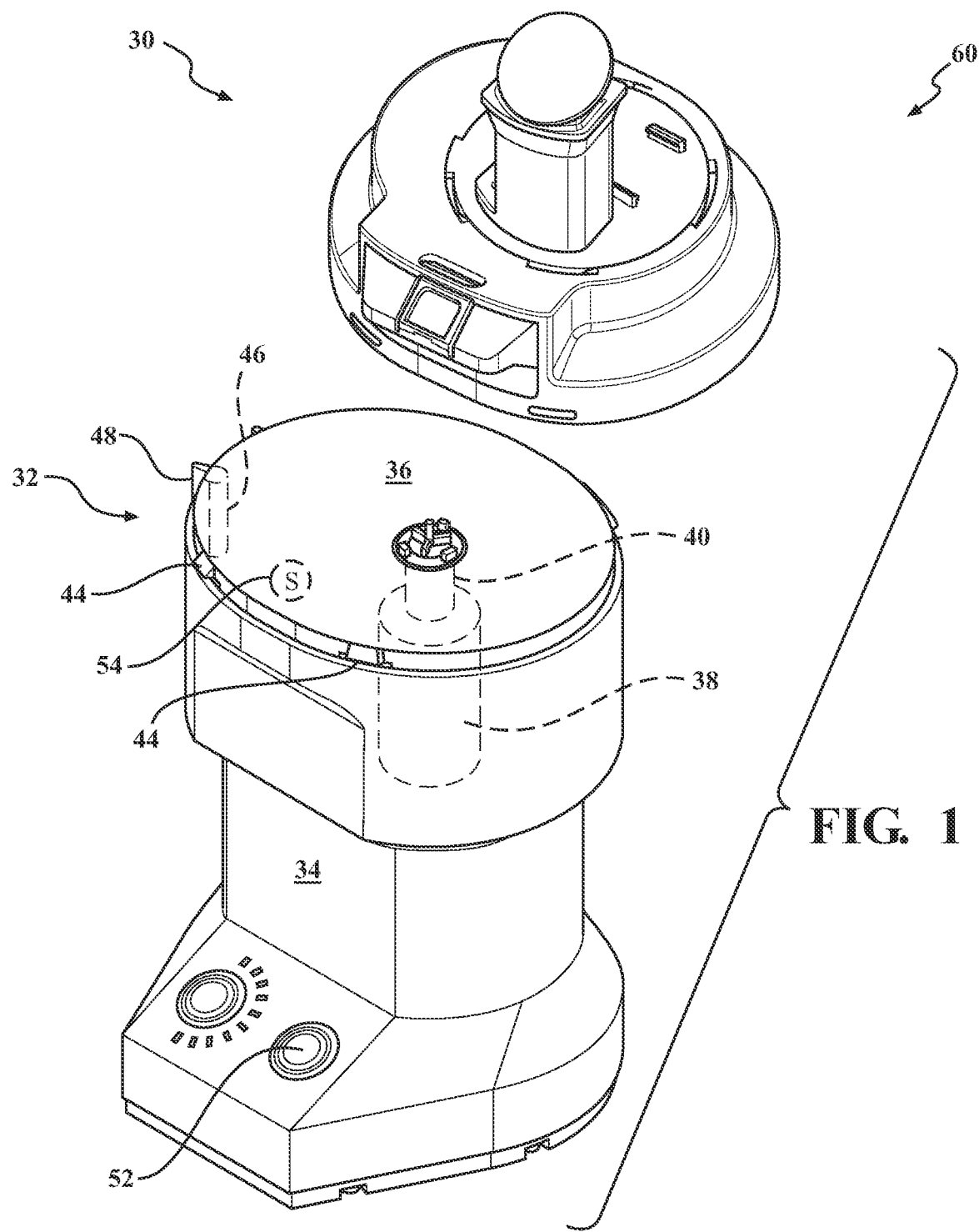
FIG. 1 is an exploded view showing how a bone mill of this disclosure is releasably mounted to a base module capable of actuating the bone mill.

The bone mill of this disclosure is constructed to ensure that, to the extent possible, the bone chips produced during the milling process are recovered. This ensures that, to the extent possible, for a given volume of bone stock that is milled, the largest volume of bone chips are available for the surgical procedure requiring the use of the bone chips.

The bone mill of this disclosure is further designed to reduce the likelihood that, in the event the bone mill is not property configured use, a milling element which is configured to convert bone stock into bone chips cannot be actuated. This to ensure substantial elimination of the possibility that, if the bone mill is not properly configured, actuation of the milling element could result in damage or physical harm.

This disclosure is directed to a bone mill that includes a housing. The housing includes at least an inlet opening. The milling element is located below the inlet opening. The milling element converts the bone stock into bone chips. In one version of the disclosure, the milling element is shaped to push bone stock against an impingement plate. The impingement plate is integral with or secured to the housing. As a result of the action of the milling element pushing bone stock against the impingement plate, the bone stock is sheared into bone chips which are smaller in size/volume than the bone stock. Most to the bone chips drop below the milling element. In many versions of the disclosure the bone chips drop into a catch tray. The catch tray is removable from the housing.

The bone mill of this disclosure is further designed so the housing consists of a foundation to which a removable lid is attached. The removability of the lid makes it possible to access the milling element. Once the lid is removed, the milling element may be removed through the opening in the foundation previously covered by the lid. In many versions of the disclosure, the milling element includes a handle.

Once bone chips are formed using the milling element of this disclosure, the lid is removed. The milling element is removed from the housing. Using an appropriate tool, such as a scraper, bone chips that adhered from to the milling element are scraped off the milling element into the container the holds the bone chips. Typically, during this part of the procedure, the person recovering the bone chips that may have otherwise been discarded typically holds the milling element by the handle.

A further feature of this disclosure is that a detection component is attached to the lid. A complementary sensor in the unit employed to actuate the cutting element detects the presence/absence of the detection component. If the presence of the detection component is not detected, the unit interprets the bone mill as being in a state in which the lid is not properly secured to the foundation. Therefore, the unit will not allow the bone mill to be actuated.

In many versions of the disclosure the container into which the bone chips fall is the void space/catch basin of a catch tray. The catch tray is removably attached to the housing. In these versions of the disclosure, the catch tray is often provided with a detection component separate from the detection component attached to the lid. In these versions of the disclosures the bone mill is designed so the detection components must be in registration with each other in order for the sensor in the drive unit to detect either detection component. If the sensor does not detect the presence of either one or both of the detection components, the bone mill will not operate. This alerts the individual performing the milling process that there is likelihood that the bone mill is in a state in which the lid is not secured to the foundation and/or the catch tray is not correctly seated in the housing.

In some versions of the disclosure, the housing is further constructed so the inlet opening is formed in the removable lid. In some versions of the disclosure the housing is further constructed so there is an outlet opening in the foundation through which the bone chips drop into the catch tray. In some embodiments of this version of the disclosure the outlet opening is at least partially in registration with the inlet opening.

In some embodiments of the disclosure, the housing includes features that facilitate the releasable coupling of the milling module to the base module that drives the milling element. In these embodiments of the disclosure, the milling element is formed with features that releasably couple the milling element to a drive spindle that actuates the milling element. Often these milling element drive features that releasably couple the milling element to the drive spindle are accessible through a specific opening in the housing that is present in part for that very purpose.

In some versions of the disclosure, the milling element is configured to rotate in the housing. In some species of this version of the disclosure, a shaft transfers the rotational movement of the drive spindle to the milling element so as to rotate the milling element. In these embodiments of the disclosure, the shaft is bi-functional. In addition to serving as a drive-link, the shaft functions as the handle that is held when the bone chips that have adhered to the milling element are being recovered.

With reference now to the drawings, wherein like numerals indicate like parts throughout the several views, a new and useful bone mill is shown at 30 in FIG. 1. The bone mill 30 is also referred to herein as the bone milling system ("system") 30. The system 30 is modular; the system 30 includes a base module 32 to which a milling module 60, sometimes called a mill head, is removably attached.

The base module 32 includes a base shell 34. The base shell 34 is the housing of the base module 32. The base shell 34 has a top surface 36. Internal to the base shell 34 is a motor 38 represented by a dashed cylinder. Also internal to the base shell 34 is a drive spindle 40. The drive spindle 40 has a head that extends through an opening in the top surface 36 of the base shell 34. The motor 38 drives the drive spindle 40. When the milling module 60 is attached to the base module 32, the drive spindle 40 engages a milling element 170. The rotation of the drive spindle 40 results in a like rotation of the milling element 170.

The base module 32 may include plural tabs 44, (two tabs seen in FIG. 1). The tabs 44 are moveably mounted to the base shell 34 so as to extend out of and back into the base base shell 34 below the top surface 36. A linkage assembly 46, represented by a single phantom bar, is disposed in the base shell 34. Normally the tabs 44 are located outwardly from the base shell 34. Linkage assembly 46 is configured cooperate with finger levers 48 to selectively retract the tabs 44 into the base shell 34. The finger levers 48, one identified, are moveably mounted to the outside of the base shell 34. The finger levers 48 are connected to the linkage assembly 46. Collectively, the tabs 44, the linkage assembly 46 and the finger levers 48 are configured so that the tabs extend outwardly. As a result of the displacement of the finger levers 48, the linkage assembly 46 retracts the tabs 44 into the base shell 34.

Figure 2:
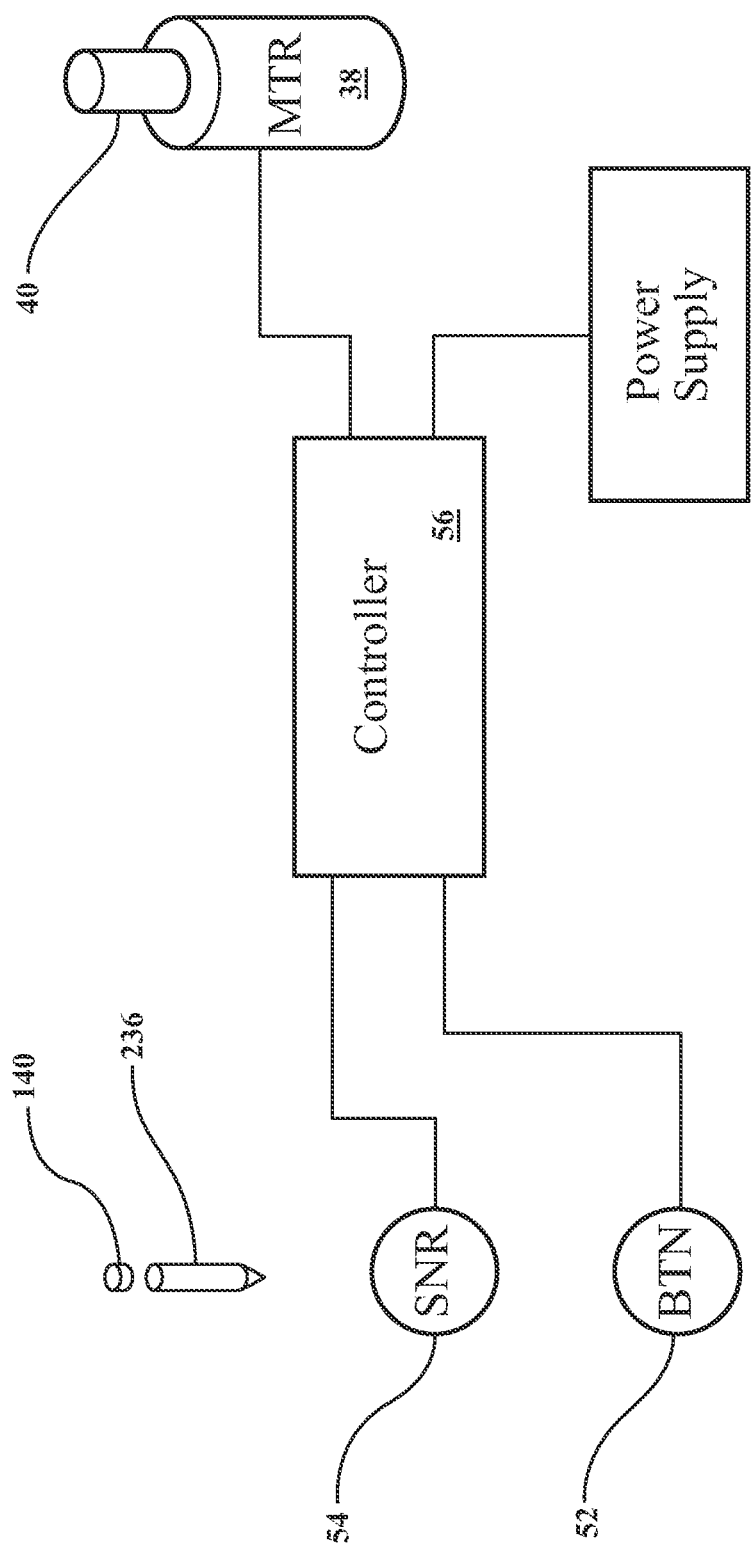
FIG. 2 is a block diagram of the electrical components of the mill of this disclosure and the markers integral with the mill head.

Also shown as mounted to base shell 34 is a control button 52. The control button 52 is part of a control circuit, the components of which are seen in FIGS. 1 and 2. The control circuit also includes a sensor 54. The sensor 54 is disposed in the base shell 34 below the top surface. In FIG. 1, the sensor 54 is seen in FIG. 1 as a phantom disc. The sensor 54 detects the absence/presence of a magnetic field or some other indicator adjacent the sensor. Thus, for example, the sensor 54 may be a hall-effect sensor. The state of the control button 52 as well as the signal output by the sensor 54 are applied to a controller 56 also disposed in the base shell 34. The controller/control unit 56 is not illustrated in FIG. 1, but is shown in the block diagram of FIG. 2. The controller 56 is connected between a power supply and the motor 38. While the power supply is shown in FIG. 2, it is understood that the specific construction of the power supply is not part of the disclosure. The controller 56 regulates the application of current to the motor 38 to actuate the motor 38. In many constructions of system 30, the controller 56 is configured to only actuate the motor 38 during time periods in which the button 52 is depressed.

Figure 3:
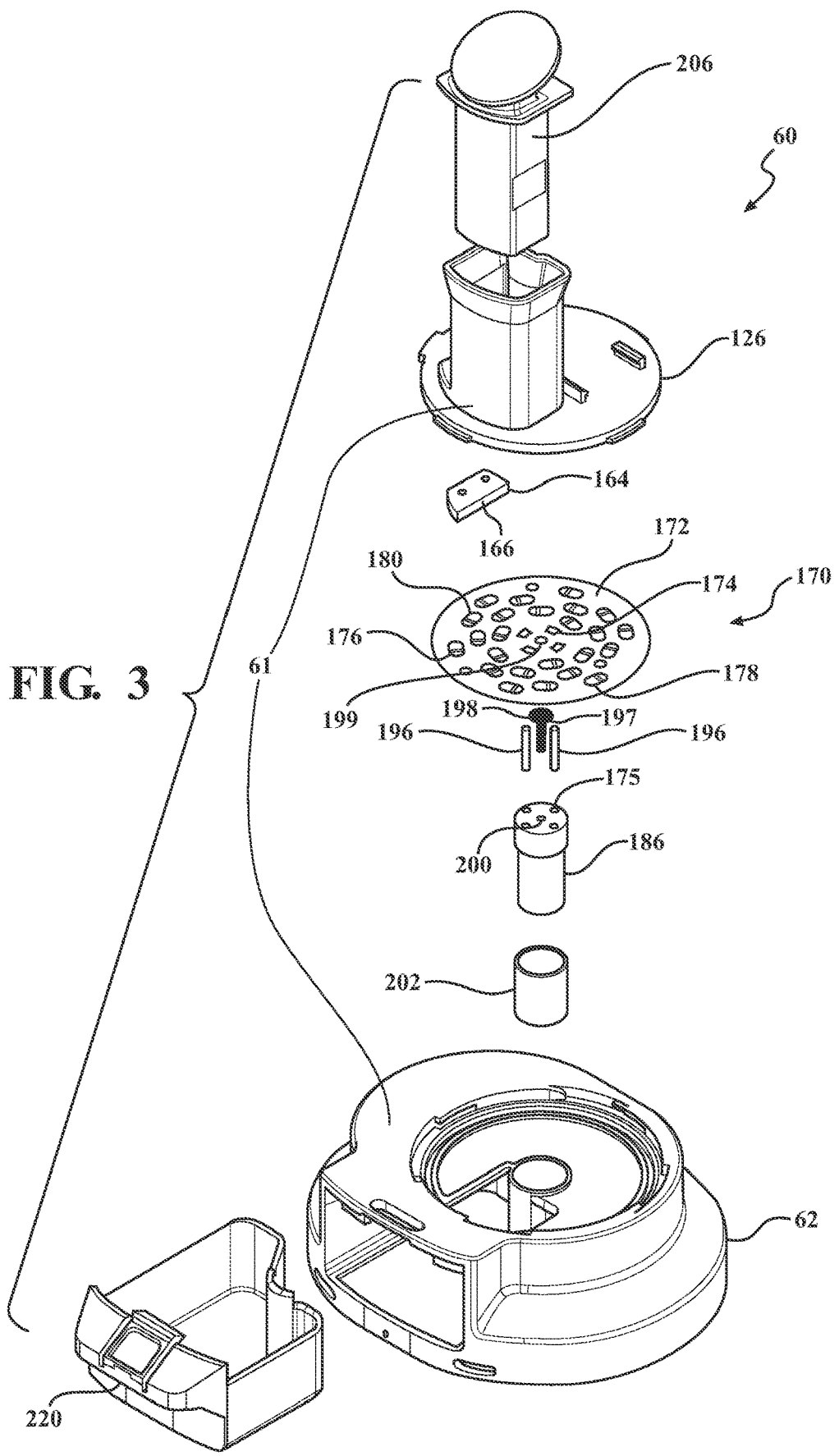
FIG. 3 is an exploded view of the bone mill of this disclosure.
Figure 5:
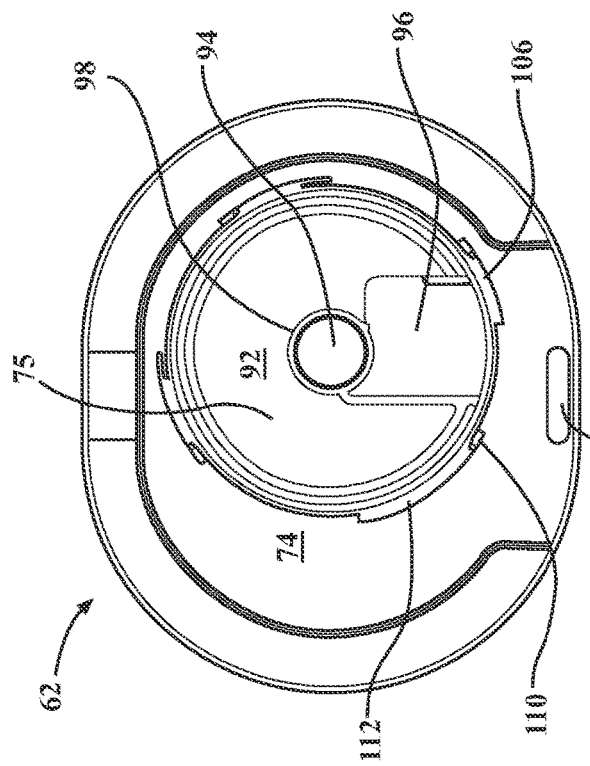
FIG. 5 is a top view of the foundation of FIG. 3.
Figure 4:
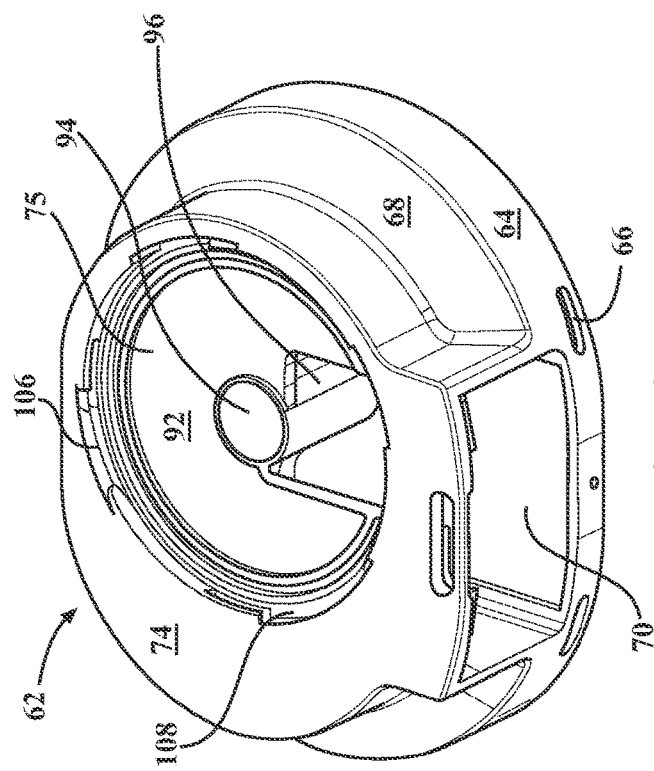
FIG. 4 is a perspective view of the foundation of the shell of the bone mill.
Figure 6:
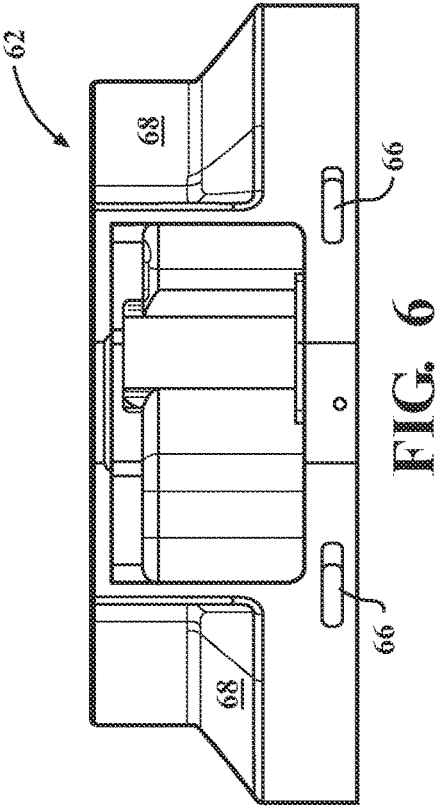
FIG. 6 is a side view of the foundation of FIG. 3.
Figure 8:
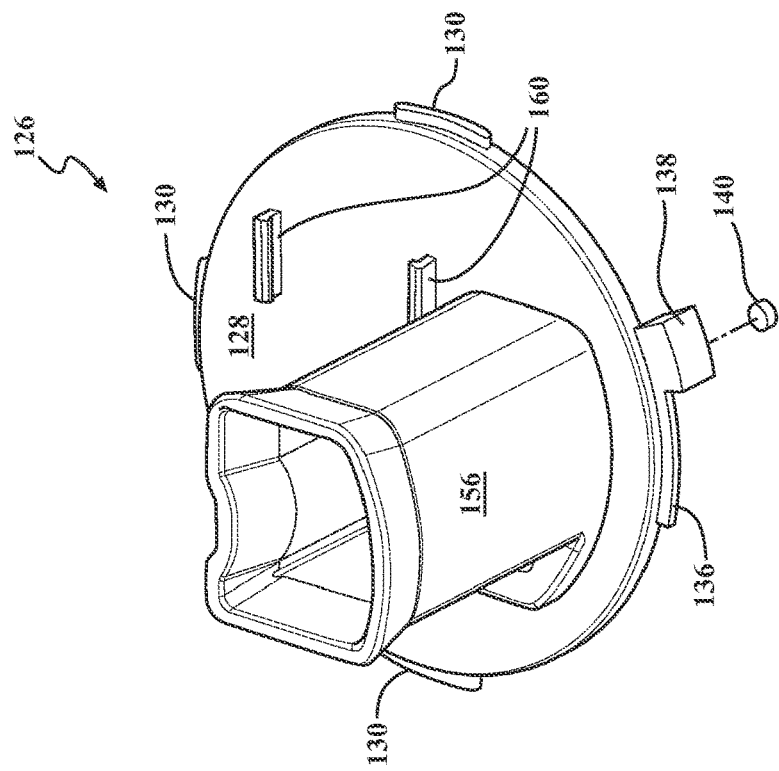
FIG. 8 is a perspective view of the lid of the shell of the bone mill.
Figure 7:
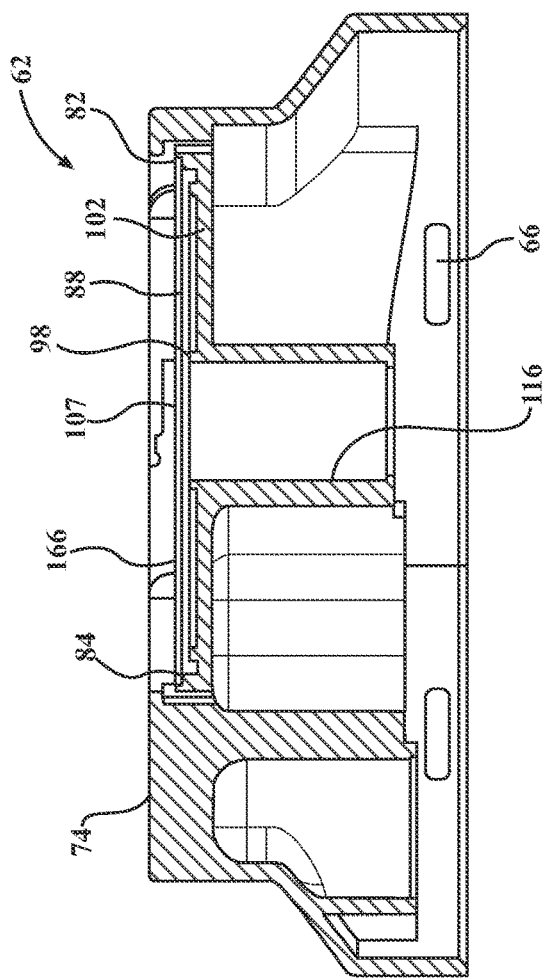
FIG. 7 is a cross sectional view of the foundation of FIG. 3.

The milling module 60, as seen in FIG. 3, includes a foundation 62 to which a lid 126 is removably attached. Collectively, the foundation 62 and lid 126 form the housing or shell 61 of the milling module 60. The shell 61 is adapted for releasable attachment to a base module 32. The shell 61 has an inlet opening 152 through which bone stock is introduced into the shell 61 and an outlet opening 96 through which bone chips are discharged from the shell 61. The milling element 170 is moveably disposed in the shell 61 between the inlet opening 152 and the outlet opening 96 for converting bone stock into bone chips. The milling element 170 includes features for removably attaching the milling element 170 to the base module motor 38 so that the actuation of the motor 38 results in the actuation of the milling element 170.

The foundation 62 of the milling module 60 is adapted for releasable attachment to the base module 32. The foundation 62, as seen in FIGS. 4-7, may include a rim 64 which forms the bottom portion of the base. Rim 64 is dimensioned to seat around the outer perimeter of the top surface 36 of base module 32. The rim 64 is formed with plural openings 66. The mill head foundation 62 is formed so that when milling module 60 is seated over the base module top surface 36, each tab 44 integral with base module 32 can seat in and extend through an opening 66. That is, the foundation 62 includes a rim 64 having plural openings 66 and is dimensioned to seat around the outer perimeter of the top surface 36 of base module 32, wherein when seated the plural tabs 44 on the base module 32 extend through the plural openings 66 to become integral with the plural openings 66 and correctly attach the milling module 60 to the base module 32. Side walls 68 extend upwardly and inwardly from rim 64. An opening 70 extends through one of the side walls 68. The base module 32 is further formed to have a top panel 74. The top panel 74 extends inwardly from the top end of the top most side wall 68. The top panel 74 is further formed to have an opening 76. Opening 76 opens into the void that extends inwardly from opening 70.

The foundation 62 of the milling module 60 is further formed to have a recessed surface 92 that may be generally circular in shape is located below the top panel 74. The foundation 62 is formed so that there are two openings in the recessed surface 92. An opening, opening 94, is circular in shape and is concentric with the center of the recessed surface 92.

The foundation 62 includes the outlet opening 96. The outlet opening 96, extends inwardly from the outer perimeter of the recessed surface 92. The outlet opening 96 opens into the void below panels 74 and 92 that extends inwardly from opening 70. A ring 98 extends upwardly from the recessed surface 92 and circumferentially surrounds opening 94. Ring 98 functions as a barrier between opening 94 and the outlet opening 96. Foundation 62 has a second ring 102 that also extends upwardly from recessed surface 92. A ring 102 is located immediately inward of the outer perimeter of the recessed surface 92. The ring 102 does not extend circumferentially around recessed surface 92. Instead, the outlet opening 96 interrupts the ring 102.

The foundation 62 may be formed with two steps 84 and 88 that the transitional structural components of the mill head that suspend recessed surface 92 from top panel 74. Steps 84 and 88 extend arcuately around the opening 75 in the top panel 74 in which the recessed surface 92 is located. The top most step, step 84, includes a riser, not identified. This riser is the structural feature of step 84 that is perpendicular to the plane of top panel 74 and, in a gravity reference plane, extends downwardly from the top panel. The riser of step 88 is the component of step 88 that extends upwardly from the outer edge of step 88 to the inner edge of step 84. The foundation 62 is formed so that step 88 is spaced radially outwardly from the ring 102. It should further be understood that relative to recessed surface 92, step 88 is located above the top surface of the ring 102.

The foundation 62 is further formed so as to have plural notches 106 that extend inwardly from perimeter of the top panel 74 that defines opening 75. Only one notch 106 is identified in each of FIGS. 4, 5 and 7. Where each notch 106 is present, the riser of step 84 is located radially outwardly of where the riser is located if the notch is not present. Also where each notch 106 is present, the adjacent step 84 extends radially outwardly of the adjacent portion of the step 84 where the notch is not present. Adjacent each notch 106 there is an indentation 107 in the riser of step 84. Each indentation 107 extends arcuately away from the end of the notch 106 with which the notch 106 is integral.

The foundation 62 is formed to have three notches 106 each with its own companion indentation 107. There is a center located notch 106 that is the notch spaced furthest away from opening 70. The notches 106 located on either side of the center located notch 106 are each spaced 90° from the center located notch. Specific notches 106 are not identified with particularity.

The foundation 62 is further formed so there is a fourth notch, notch 108, that extends outwardly from the portion of the top panel 74 that defines opening 75. Notch 108, is formed in the foundation 62 so, relative to opening 94, is diametrically opposed to the center located notch 106. The foundation 62 is formed so notch 108 interrupts riser 82 and step 84. A panel 110 defines the base of notch 108. The panel 110 extends between an inner surface of the side panel that is located radially outwardly from riser 82 integral with step 84 and the outer surface of the riser 86. Panel 110 does not extend below the whole of the base of the notch 108. Instead, there is an opening 112 in panel 110. The opening 112 is located so as to provide a portal from notch 108 into the void space that extends inwardly from opening 70.

The foundation 62 is further formed to have a tube-like sleeve 116 that extends downwardly from the recessed surface 92. More particularly, sleeve 116 extends downwardly from recessed surface 92 so as to extend around the portion of the panel that defines the perimeter of opening 94. System 30 is designed so that when milling module 60 is attached to the base module 32, surface 92 and sleeve 116 are coaxial with drive spindle 40.

The foundation 62 also includes the lid 126. The lid 126 is removably attached to the foundation 62. The lid 126 includes the inlet opening 152 of the shell 61. The foundation 62 and the lid 126 are collectively configured so that removal of the lid 126 from the foundation 62 allows the milling element 170 to be accessed. As is described in detail below, the milling element 170 is removably attached to the foundation 62 of the shell 61.

The lid 126, best seen in FIGS. 8-11, includes a disc shaped cap 128 defines an inner surface 129. In one embodiment, the disc shaped cap 128 is domed. Cap 128 is shaped to fit in opening 75. More particularly, the outer perimeter of the cap 128 is dimensioned to seat on step 84. The cap 128 includes one or more tabs 130 that project radially outwardly from a cylindrical side wall 131 of the cap 128. The one or more tabs 130 are positioned and dimensioned so that when the cap 128 is positioned in an opening 75 in the foundation 62 and rotated, each tab 130 rotates into a respective notch 106 in the foundation 62 to become integral with the notch 106 and correctly attach the lid 126 to the foundation 62. For example, in the embodiment shown three tabs 130 project radially outwardly from the cylindrical side wall 131 of the cap 128. The tabs 130 are positioned and dimensioned so that when the cap 128 is seated in the opening 75, each tab 130 seats in and is able to rotate in a separate one of the notches 106. That is, the components forming the bone mill are shaped so that cap 128 can rotate into opening 75, and so that when the lid 126 is rotated, the tabs 130 are able to rotate into the notches 106 and become integral with the notches 106.

A fourth tab, tab 136, extends radially outwardly from the cylindrical side wall 131 of cap 128. Foundation 62 and lid 126 are collectively constructed so that when cap 128 is seated in opening 75, tab seats in and is able to rotate in notch 108. A toe 138 extends downwardly from one end of tab. The foundation 62 and lid 126 are further shaped so that when cap 128 rotates the reduced height sections 134 sit in the notches 106 to seal the bone cleaning chamber, and the toe 138 moves into registration over opening 112 in the foundation so that the bone mill 30 can be used.

A first detection component 140, e.g. the magnet, is disposed in an opening in the toe 138 (opening not identified). That is, one of the one of the one or more tabs 130 includes the toe 138 having the magnet 140 disposed therein and extending downwardly from one end of tab 130, wherein when the cap 128 is positioned in the opening 75 in the foundation 62 and rotated to correctly attach the lid 126 to the foundation 62, the toe 138 moves into registration over an opening 112 in the foundation 62 when the lid 126 is correctly attached to the foundation 62. Other locations of the first detection component are also contemplated.

The cap 128 includes one or more rings 142, 144, and 146 which extend downwardly from the inner surface 129 of the cap 128. Each of the rings 142, 144 and 146 is concentric with the cap 128. Ring 142 is the innermost ring. The lid 126 is shaped so that when the lid 126 is seated on the foundation lid ring 142 is spaced no more than ±2 mm from the space subtended by ring 98 integral with the foundation 62. Typically ring 142 at least partially, if not completely, overlaps ring 98. Ring 144 is the intermediate ring. Ring 144 is located radially outwardly of the ring 142. The lid 126 is shaped so that when the lid 126 is seated on the foundation, ring 144 is spaced no more than ±2 mm from the space subtended by ring 102 integral with the foundation 62. Typically ring 144 at least partially, if not completely, overlaps ring the 102. Ring 146 is located radially outwardly of ring 146.

The components forming the milling module 60 are shaped so that when the lid 126 is fitted to the foundation 62, ring 146 seats against step 88. That is, the outermost ring 146 is positioned on an outer perimeter of the cap 128, and seats against a step 88 on the foundation 62 when fitted thereto.

The cap 128 includes one or more ribs 143, 145 extending downwardly from its inner surface 129, the ribs 143, 145 are configured to push bone stock into a cutting disc 172 of the milling element 170 and prevent bone stock from accumulating on the inner surface 129 of the cap 128 or on the surface of the cutting disc 172 when the bone mill 30 is in operation. In some embodiments, at least one rib 145 extends inwardly from the intermediate ring 144 and angles away from the location on the intermediate ring 144 from which the rib 145 extends, but does not extend to the innermost ring 142, wherein the at least one rib 143 curves in the direction of rotation of the cutting disc 172. Further, in some embodiments, at least one rib 143 extends inwardly from the innermost ring 142 and angles away from the location on the innermost ring 142 from which the rib 145 extends, but does not extend to the intermediate ring 144, wherein the at least one rib 143 curves in the direction of rotation of the cutting disc 172.

Figure 11:
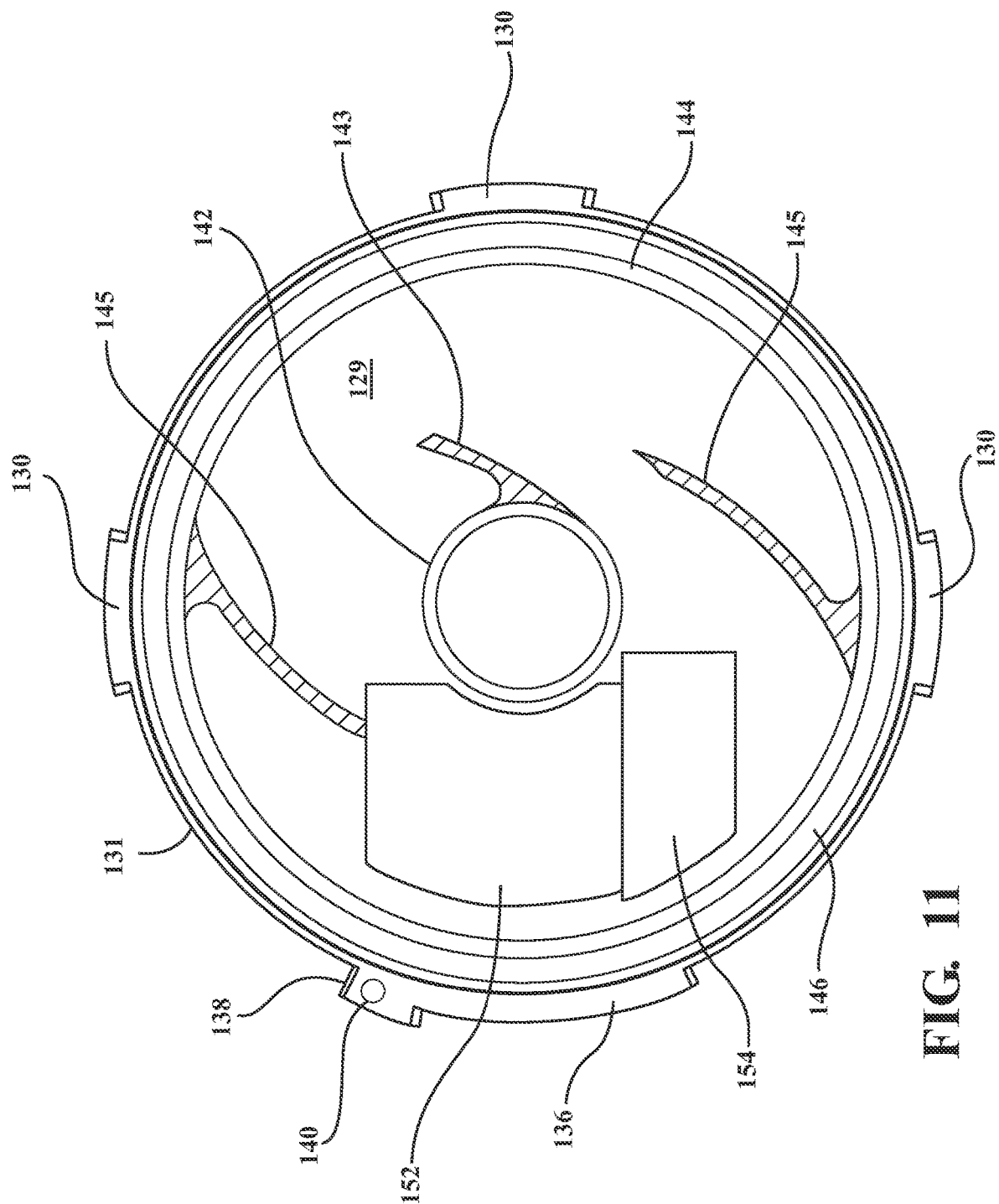
FIG. 11 is a bottom plan view of the lid.

In FIG. 11, a rib 143 extends outwardly from ring 142. As rib 143 extends outwardly, the rib angles away from the location on the ring from which the rib extends. Two ribs 145 extend inwardly from ring 144. As each rib 145 extends inwardly, the rib curves away from the point on the ring 144 from which the rib extends. In the illustrated version of the disclosure, rib 143 does not extend to ring 144. Ribs 145 do not extend to ring 142. Each of the ribs 143 and 145 are understood to project downwardly from the inner surface of cap 128. Each rib 143 and 145 is understood to curve clockwise away from the associated ring 142 and 144, respectively. More particularly, each rib 143 and 145 curves in the direction of rotation of the cutting disc 172 and towards the portion of the center ring of cutting scallops 176 on the cutting disc 172.

In a number of versions of the disclosure, the distance each rib 143 and 145 extends downwardly from the inner surface 129 of cap 128 is less than the distance the associated ring 142 and 144, respectively, extend downwardly from the same surface. In some versions of the disclosure, as each rib 143 and 145, extends away from the associated ring 142 and 144, respectively, the extent to which the rib extends downwardly from the cap. Thus, adjacent the ring from which a rib extends, the rib has its maximum height. Extending away from the ring 142 or 144, the height of the rib 143 or 145 decreases. A first one of the ribs 145 extends to the inlet opening 152. Rib 143 and the second rib 145, the rib 145 that terminates away from the inlet opening 152, each tapers into a point.

The cap 128 is also shaped to have the inlet opening 152. The cap 128 is formed so that when the cap is located to the foundation 62, the inlet opening 152 is in registration with and located above opening 94. The cap 128 is also formed to have a void space 154. Void space 154 extends upwardly from an inner surface 129 of the cap 128 which boarders the inlet opening 152.

Lid 126 also includes a feed sleeve 156. Feed sleeve 156 extends upwardly from the outer surface of the cap 128 and surrounds the inlet opening 152.

Two parallel brackets 160 are also part of the lid 126. Brackets 160, like the feed sleeve 156, extend upwardly from the outer surface of the cap 128. Each bracket 160 is L-shaped. More specifically the long section of each bracket 160 extends upwardly from the cap 128. The short sections of each bracket 160, the sections perpendicular to the long sections, are directed towards each other. A stop 162, seen only in FIG. 9, also extends upwardly from cap 128. Lid 126 is formed so that the stop 162 extends upwardly from a location that is in registration with the space between the brackets 160 and spaced away from the space between the brackets. Stop 162 is planar in in a shape and located in a plane that is perpendicular to the parallel planes of the long sections of the brackets 160.

An impingement plate 164, seen only in FIG. 3, is rigidly mounted to the lid 126. More particularly, the impingement plate 164 is secured in the void space 154 internal to the cap 128. The components forming the milling module 60 are constructed so that the impingement plate 164 has a surface 166 that is located immediately below the perimeter of the inlet opening 152 in the cap 128.

The milling element 170 of mill head 6, seen only in FIG. 3, includes a circularly shaped planar cutting disc 172. Other shapes of the milling element 170 are also contemplated, i.e., non-circular shapes. Located around the center of the cutting disc 172 are four equiangularly shaped apart openings 174, only one opening identified. The cutting disc 172 includes features that convert bone stock into bone chips. That is, the cutting disc 172 is further formed to have a number of cutting scallops 176, one identified. Integral with and longitudinally axially aligned with each cutting scallop 176, the cutting disc has a through opening 180. More particularly, the cutting disc 172 is formed so that each cutting scallop 176 extends above the planar top surface of the element. The scallops 176 are milled to define cutting edges 178, one cutting edge identified. Each cutting edge 178 partially defines the parameter of the adjacent opening 180.

Figure 13:
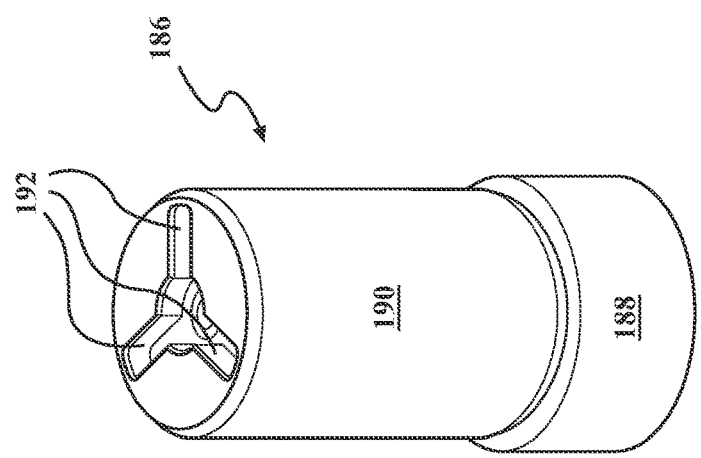
FIG. 13 is a perspective view of the bottom of the shaft to which the milling element is attached.
Figure 12:
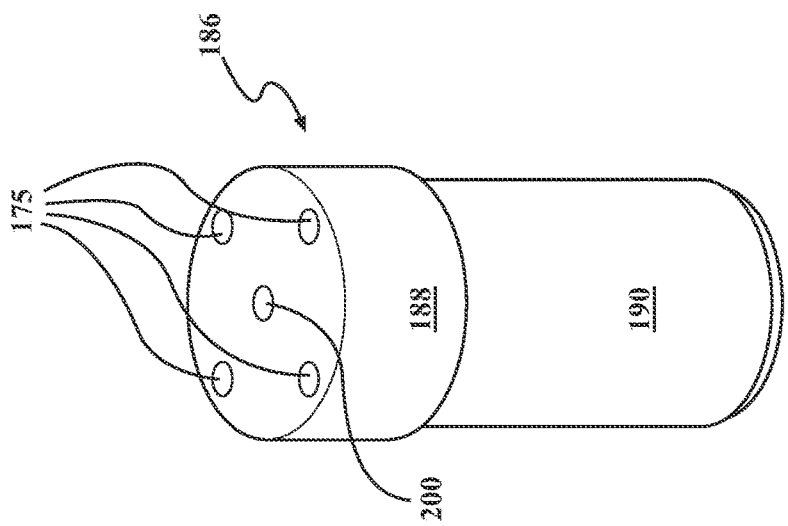
FIG. 12 is a perspective view of the top of the shaft to which the milling element is attached.
Figure 15:
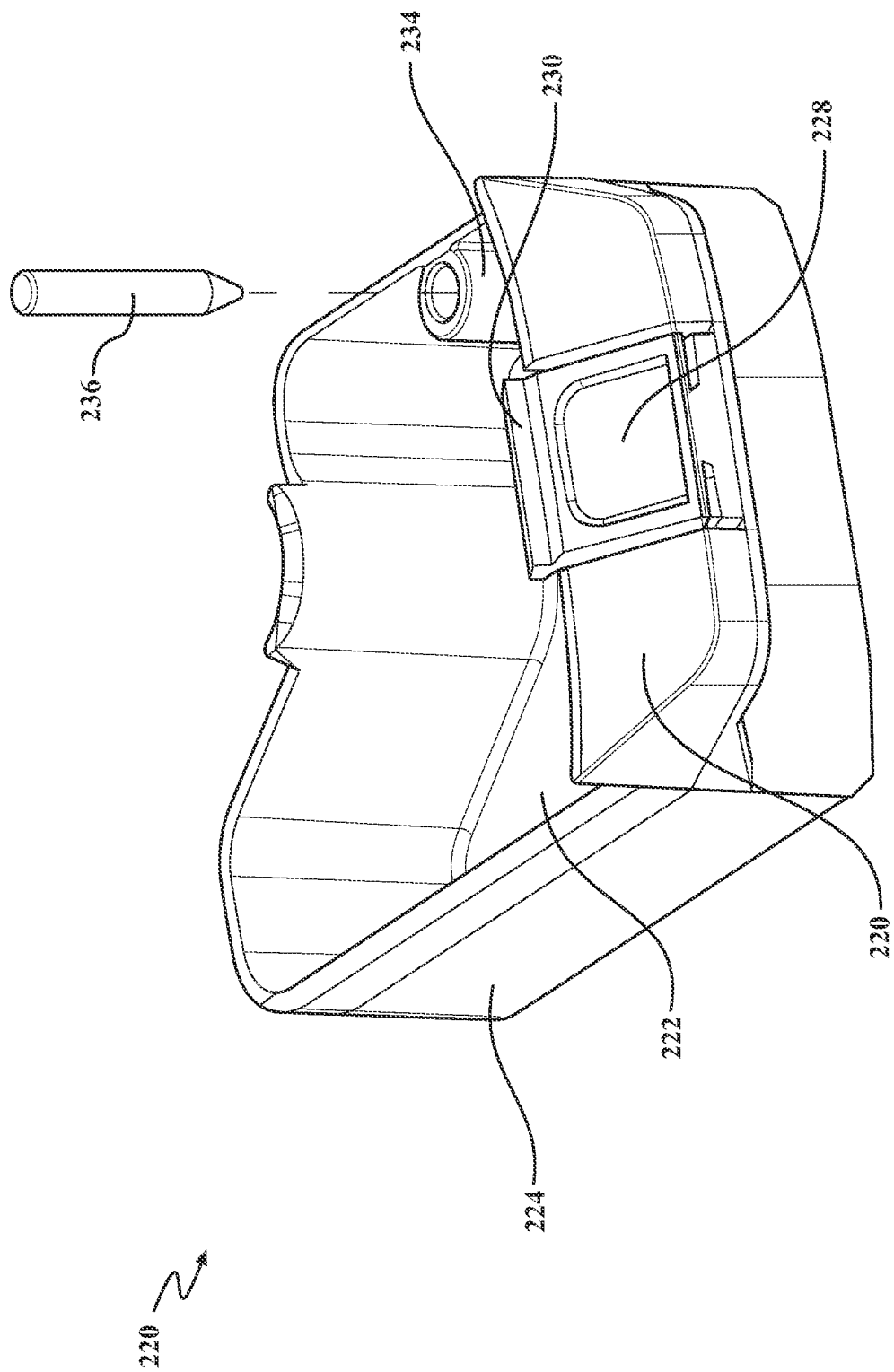
FIG. 15 is a perspective view of the catch tray and the marker that is attached to the catch tray.

A shaft 186, also part of the milling element 170, seen best in FIGS. 12 and 13, extends downwardly from the center of the cutting disc 172. In a typical embodiment, the shaft 186 is permanently attached to the cutting disc 172. The shaft 186 is configured to connect to the cutting disc 172 and the drive spindle 40 and remains attached to the cutting disc 172 during removal of the milling element 170 from the foundation 62 and is adapted to be held. To this end, the shaft 186 extends from the cutting disc 172 and is formed with the features 192 that removably couple the milling element 170 to the motor 38 of the base module 32. The shaft 186 is generally cylindrical in shape. The shaft 186 is formed to have a head 188. The shaft head 188 has a diameter that allows the head to seat in and rotate in sleeve 116 integral with the foundation 62. A cylindrical stem 190 extends below the head 188. Stem 190 has a diameter less than that of the head 188. The bottom end of the stem 190 the end that faces drive spindle 40 is formed with a feature for releasably engage the spindle. In one embodiment, the stem 190 includes one or more notches 192 that extend upwardly from a bottom face of the stem 190 and are spaced radially outwardly from the center of the stem 190, wherein the one or more notches 192 are configured to engage one or more complementary teeth on a face of the drive spindle 40 of the base module 32 so that the rotation of the drive spindle 40 results in the like rotation of the milling element 170. For example, in the illustrated version of the disclosure this feature consists of three equiangularly spaced apart notches 192 that extend upwardly from the base of the stem 190. Referring now to FIG. 3, the cutting disc 172 includes at least one opening 174 spaced radially outwardly from the center of the cutting disc 172 that aligns with a complementary hole 175 on the head 188 of the shaft 186. In FIG. 3, four off-center openings 174 correspond to four corresponding off-center opening 175 (also shown in FIG. 12). At least 1 pin 196, two of which are shown in FIG. 3, is operatively inserted through each opening 174 and into the complementary hole 175 so that the rotation of the shaft 186 results in the like rotation of the cutting disc 172. These plural pins 196, two of which are identified in FIG. 3, extend upwardly from the top surface of shaft head 188 and through the openings 174 off-center on the cutting disc 172. A central pin 197 having a head 198 is inserted into a central opening 199 on said cutting disc. In embodiments where the central pin 197 is inserted in the central opening 199, the central pin 197 extends into a central hole 200 on the shaft 186. As such, the central pin 197 holds the shaft 186 to the cutting disc 172.

A tube shaped bushing 202, seen only in FIG. 3, extends between the outer surface of shaft stem 190 and the inner surface of sleeve 116. Bushing 202 is formed from a low friction polymer such as polyoxyethylene, UHMW plastic, Nylon, PEEK or semicrystalline PET. The bushing 202 functions as a low friction interface between the static sleeve 116 and the rotating shaft 186.

In some embodiments, the milling element 170 also includes a spring 187 that cooperates with the shaft 186. In such embodiments, the shaft 186 and the spring 187 are collectively configured so that when the lid 126 is not attached to the foundation 62: the shaft 186 will not attach to the drive spindle 40; the shaft 186 will not engage the cutting disc 172; or the shaft 186 will not operatively function, such that the milling element 170 and/or cutting disc 172 cannot be actuated if the lid 126 is not correctly attached to the foundation 62.

Figure 16B:
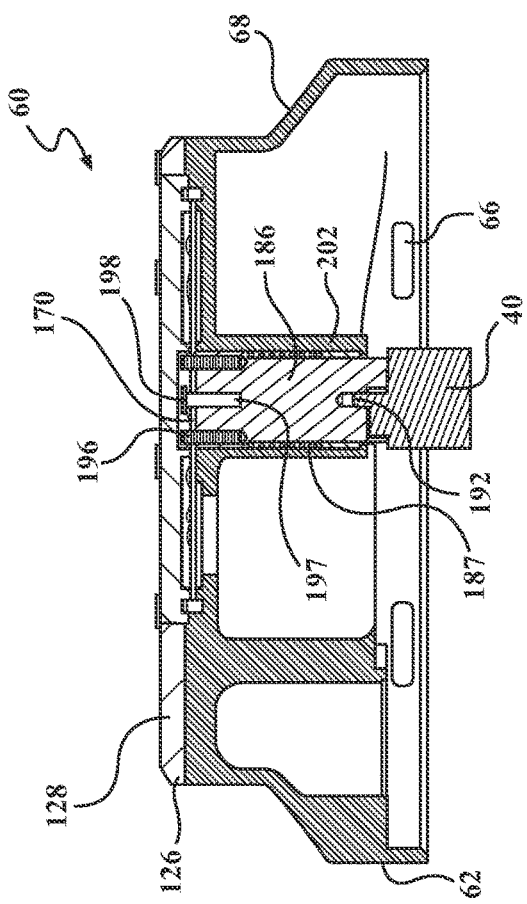
FIG. 16B is a cross sectional view along line A-A of the milling module of FIG. 16A.
Figure 16A:
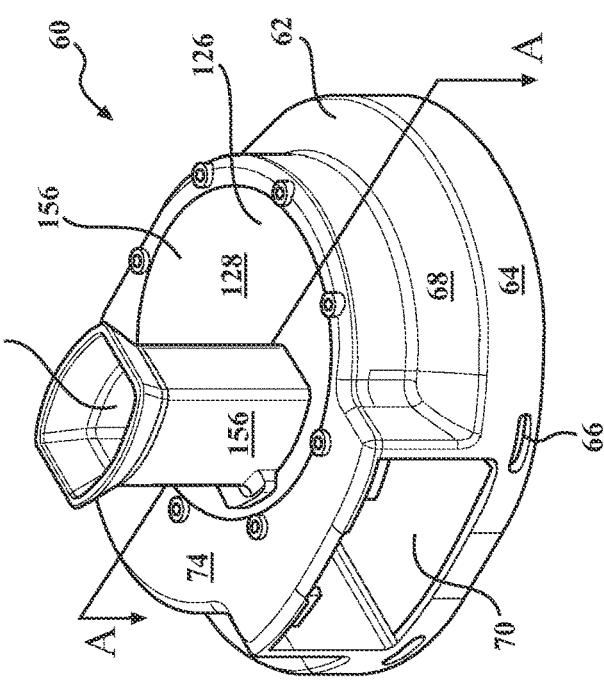
FIG. 16A is a perspective view of a milling module including a lid attached to a foundation, and having a cutting element therebetween which includes a cutting disc, a shaft, and a spring.
Figure 18C:
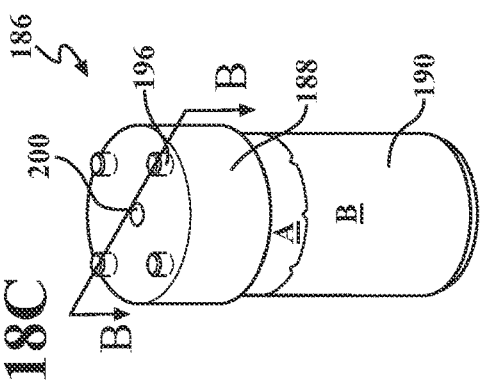
FIG. 18C is an enlarged perspective view of the shaft and the spring of FIGS. 18A and 18B.
Figure 18D:
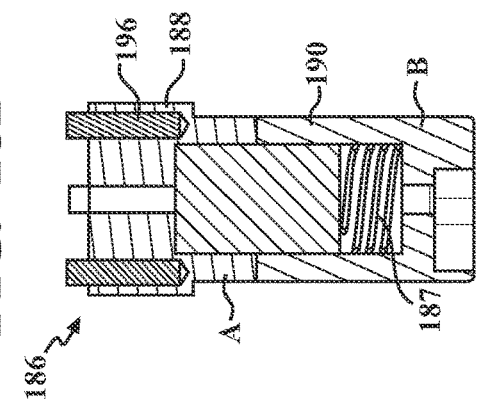
FIG. 18D is a cross sectional view along line B-B of the shaft and the spring of FIG. 18C.
Figure 18B:
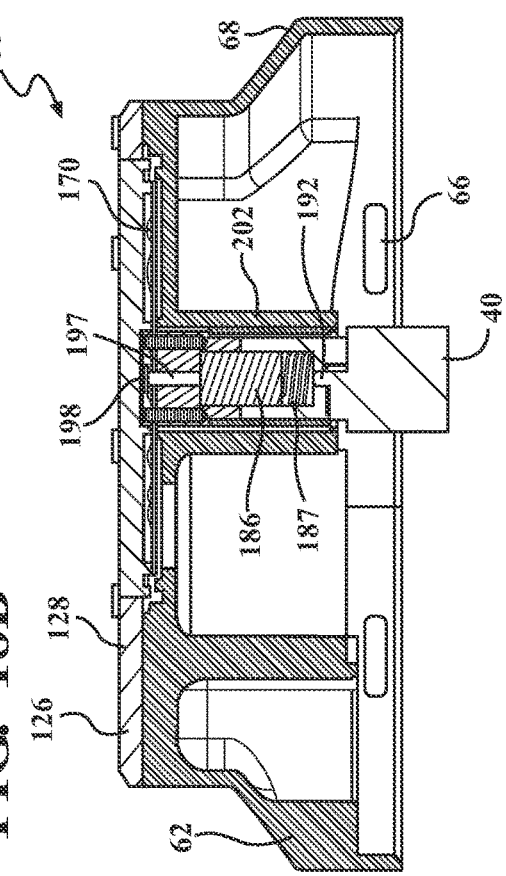
FIG. 18B is a cross sectional view along line A-A of the milling module of FIG. 18A.
Figure 18A:
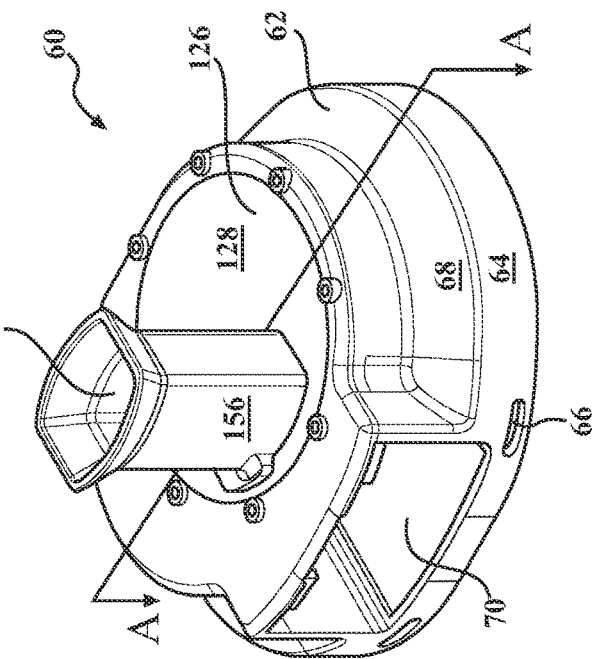
FIG. 18A is a perspective view of a milling module including a lid attached to a foundation, and having a cutting element therebetween which includes a cutting disc, a shaft, and a spring.

For example, in the embodiment of FIGS. 16 and 17, the spring 187 is disposed between an exterior surface of the shaft 186 and the bushing 202, and the shaft 186 and the spring 187 are collectively configured so that when the lid 126 is not attached to the foundation 62: the shaft 186 will not attach to the drive spindle 40. FIGS. 16A and 16B show the milling module 60 with the lid 126 properly attached to the foundation 62 and the shaft 186 engaged with the drive spindle 40 via the features 192 for removably attaching the milling element 170 to the base unit motor 38 so that the actuation of the motor results in the actuation of the milling element 170. That is, in FIG. 16B the one or more notches 192 engage one or more complementary teeth on a face of the drive spindle 40 of the base module 32 so that the rotation of the drive spindle 40 results in the like rotation of the milling element 170 so long as the lid 126 properly attached to the foundation 62. In contrast, FIGS. 17A and 17B show the milling module 60 with the lid 126 not attached to the foundation 62 and thus the shaft 186 is not engaged with the drive spindle 40 via the feature 192 for removably attaching the milling element 170 to the base unit motor 38 so that the actuation of the motor does not result in the actuation of the milling element 170. That is, in FIG. 17 the one or more notches 192 do not engage one or more complementary teeth on a face of the drive spindle 40 of the base module 32 so that the rotation of the drive spindle 40 results in the like rotation of the milling element 170 because the lid 126 is not properly attached to the foundation 62.

As another example, in the embodiment of FIGS. 18 and 19, the spring 187 is disposed within the shaft 186, and the shaft 186 includes a first portion A and a second portion B. In this embodiment, the portions A and B cooperate to insure that the shaft 186 will not operatively function and the cutting disc 172 cannot be actuated if the lid 126 is not correctly attached to the foundation 62. In this embodiment, the shaft 186 and the spring 187 are collectively configured so that portions separate when the lid 126 is not attached to the foundation 62, and the milling element 170 cannot be actuated because the shaft cannot transfer rotational movement from the drive spindle. FIGS. 18A-D show the milling module 60 with the lid 126 properly attached to the foundation 62 and the first portion A and the second portion B configured such that the actuation of the motor results in the actuation of the cutting disc 172. In contrast, FIGS. 19A-D show the milling module 60 with the lid 126 not attached to the foundation 62 and the first portion A and the second portion B are not configured, and the actuation of the motor 38 and drive spindle 40 will not result in the actuation of the cutting disc 172.

Figure 14:
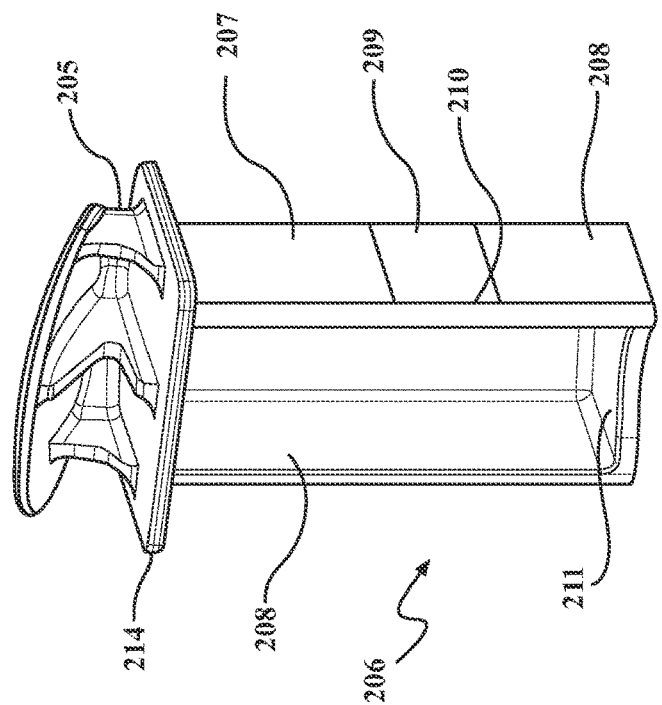
FIG. 14 is a perspective view of the plunger of the bone mill.

A plunger 206, seen in FIGS. 3 and 14, may be slidably mounted in feed sleeve 156 of the lid 126. The plunger 206 is formed to have a head 205 from which a rod 207 extends. Rod 207 is shaped to have two parallel side panels 208 and a front panel that extends between the side panels. Each side panel 208 is formed with a recessed section 209, that is located inwardly the outer surfaces of the panel on either side of the recessed section, one recessed section seen in FIG. 13. Recessed sections 209 do not extend the complete edge-to-edge widths of the side panels 208. Thus owing to the presence of the recessed section, one edge of each side panel is formed to have a step 210, the edge of one step 210 being identified in FIG. 13. Each step 210 extends inwardly from the edge of the side panel to the recessed section 209 integral with the side panel. A bottom plate 211 extends between the side panels 208 and front panel to form the base or bottom of the rod 207. Rod 207 is dimensioned to slidably fit in the housing feed sleeve 156. The rod is further formed so the recessed sections 209 of side panels 208 can snap fit between brackets 160.

The plunger 206 also includes a top plate 214. The plunger 206 is formed so that the top plate 214 extends over and projects beyond the side panels 208 and front panel, respectively. More specifically, the top plate 214 is dimensioned to subtend an area larger than the cross-sectional area of the center void of the housing feed sleeve 250. The top plate 214 thus limits the extent to which the plunger rod 207 can be pushed into the sleeve and the inlet opening 152.

A catch tray 220 is slidably disposed in the opening 70 formed in the foundation 62 of the milling module 60. That is, the catch tray is removably mounted adjacent the outlet opening to receive bone chips discharged therethrough. The catch tray 220, now described by reference to FIG. 14, has a base 222 from which a set of panels 224 extend upwardly, three panels identified. A handle 226 projects outwardly from the outermost panel 224, the panel seen when the catch tray is seated in the milling module 60. Handle 226 extends in front of the panel with which the lip is associated. Handle 226 functions as the portion of the catch tray the user grasps to insert the tray in and remove the tray from the mill head. A latch 228 is pivotally mounted to handle 226. Latch 228 includes a tab 230 that projects above the handle 226. When the catch tray 220 is seated in milling module 60, tab 230 seats in opening 76 formed in the foundation 62 as to removably hold the catch tray to the milling module 60.

Also part of the catch tray is a hollow sleeve 234. The sleeve 234 extends upwardly from the base 222 along one of the panels 224 that extends inwardly from the outermost panel 224. A second detection component 236, e.g. a rod, with high magnetic permeability is press fit or otherwise statically secured in the sleeve 234. In a typical embodiment, the second detection component 236 is a component formed from magnetically permeable material around which magnetic fields will develop. Material from which the rod 236 may be formed is 410 stainless steel or silicon core iron. Rod 236 is shaped so the end of the rod adjacent base 222 is pointed. The components forming the milling module 60 are formed so that when the lid 126 is correctly secured to the foundation and the catch tray is disposed in the foundation 62, rod 236 is located below magnet 140 (i.e., the first detection component is above the second detection component). That is, in some embodiments, the second detection component 236 of the foundation 62 is attached to the catch tray 220 and is positioned to only be in registration with the detection component 140 of the lid 126 when the catch tray 220 is correctly mounted to the foundation 62. In other words, in certain configurations, the first detection element emits a magnetic field that is propagated through the second detection element to the sensor in the base module. Thus, if the second detection element is not properly aligned to the first detection element, the magnetic field is not propagated to the sensor in the base module.

The subject disclosure also includes a method of converting bone stock into bone chips with the modular bone mill system 30 described above, which includes the base module 32 and the milling module 60.

System 30 of this disclosure is prepared for use by connecting the base module 32 to the power supply. Milling module 60 is fitted over the top surface 36 of the base module 32. As a result of this positioning of the milling module 60, the linkage assembly 46 causes the tabs 44 to first retract and then seat in openings 66 formed in the milling module 60. The seating of tabs 44 in openings 66 releasably holds the milling module 60 static to the base module 32. The lid 126 and the catch tray 220 are checked to make sure that they are correctly attached and seated. Once the milling module 60 is fitted to the base module 32 and the lid 126 and the catch tray 220 are correctly mounted in place, the system 30 of this disclosure is ready for use. That is prior to use, the method optionally includes the step of attaching the milling module 60 to the base module 32. Of course, the lid 126 should be attached to the foundation and the catch tray 220 should be mounted on the base module 32 adjacent the outlet opening 96 to receive bone chips discharged through the outlet opening 96.

In many embodiments, the first detection component 140 mounted to the lid 126 is positioned to be detectable by a sensor 54 in the base module 32 when the lid 126 is correctly mounted to the shell 61, and the second detection component 236 is mounted to the shell 61 is positioned for detection by the sensor 54 in the base module 32 when the foundation 62 is correctly attached to the base module 32.

In a typical embodiment, the first detection component 140 is mounted to the lid 126 and the second detection component 236 is mounted to the shell 61, e.g. in a catch tray 220. In order for the first and second detection component 140, 236 to be detected by the single sensor 54 in the base module 32, the first and second detection component 140, 236 must be in registration with each other. If the detection components 140, 236 are in registration with each other and detectable by the sensor 54, the catch tray 220 must be correctly seated in the foundation 62, and the foundation 62 must be correctly attached to the base module 32.

To use the system 30, bone stock is put in the feed sleeve 156. That is, the method includes the step of introducing bone stock into the inlet opening so that the milling element 170 can convert bone stock into bone chips. The plunger 206 can then be placed in the feed sleeve 156 over the bone stock.

Once these steps are completed, button 52 or other control element is depressed to actuate the system. That is, the method includes the step of actuating the milling element 170. The method also includes the step of introducing bone stock through the inlet opening into the shell 61.

As is described above, in some embodiments, the bone milling module 60 includes the first detection component 140 on the lid 126 and the second detection component 236 on the shell 61 which are detectable by the sensor 54 in the base module 32. In such embodiments, the lid 126 must be correctly attached to the foundation 62, the catch tray 220 must be correctly seated in the foundation 62, and the milling module 60 (or foundation 62 thereof) must correctly attached to the base module 32 for both detection components 140, 236 to be detectable by the sensor 54 in the base module 32. If the sensor 54 in the base module 32 detects the both detection components 140, 236 in proper position relative to one another, i.e., the milling element 170 can be actuated. In other words, to actuate the milling element 170, the lid 126 must be is correctly attached to the foundation 62, the catch tray 220 must be correctly seated in the foundation 62, and the milling module 60 (or foundation 62 thereof) must be correctly attached to the base module 32.

There may be a possibility that when use of the system 30 is wanted, the system is in a state in which the lid 126 is not secured to the foundation 62 or the catch tray is not properly positioned in the foundation. If the system is in either state, the magnetic field propagated by magnet 140 is not propagated towards sensor 54. The signal from the sensor therefore does not indicate that a magnetic field is not present adjacent the sensor. Controller 56 interprets this signal as indicating milling module 60 is not properly configured for configuration. The controller 56 therefore, in response to the depression of the button 52 will not supply an energization current to the motor 38. The failure of the system to run serves as a que to the person using the system that the position of the lid 126 and catch tray 220 need to be checked. It should be understood that in certain configurations, if the catch tray is positioned properly with respect to the foundation, the second detection element is not detectable by the sensor. This is because the second detection element is not a magnet, and thus, not separately detectable by the sensor. Thus, the second detection element only becomes detectable when the first detection element is properly positioned with respect to the second detection element, such that the magnetic field generated by the first detection element is channeled through the second detection element to the sensor.

Normally though, when system 30 is configured for use, lid 126 is properly secured to foundation 62 and the catch tray 220 seated in opening 70. If the milling module 60 is in this state, magnet 140 is disposed over rod 207 and the rod 207 is disposed over the sensor 54. When system 30 is in this state, the magnetic field emitted by the magnet 140 propagates along the outer surface of the rod 207. The magnetic field is thus present vicinity of the sensor 54. Sensor 54 thus transmits a signal to controller 56 indicated that the magnetic field is detected. Controller 56 interprets the receipt of this magnetic field present signal as being an indication that the lid is properly secured to the foundation 62 and the catch tray is properly fitted to the foundation. If the controller 56 determines the system 30 is in this state, the controller, when button 52 is depressed will source current from the power supply to the motor 38. The resultant actuation of the motor results in the rotation of the milling element 170.

The force of the plunger 206 causes the plunger to push the bone stock against the disc 172. When the cutting disc 172 rotates, the bone stock is therefore pressed between the 4 cutting edges 178 of the cutting scallops and the impingement plate. The movement of the cutting edges against the static bone stock therefore shears the bone stock into smaller sized bone chips. Gravity causes a large fraction of the bone chips to fall through the openings 180 in the cutting disc and outlet opening 96 in the foundation and into the catch tray 220.

During the milling process, some of the bone chips formed may not immediately fall through the openings 180 in the cutting disc 172. These bone chips rotate with the cutting disc 172. As these bone chips rotate, they come in contact with either of the ribs 145, 143. The chips that come into contact with the rib 145 slide along the inner surface of the rib, the surface directed towards the center of the cap 128. As a result of the continued rotation of the cutting disc, these chips come into contact with the outer surface of rib 143, the surface of rib 143 directed away from the center of cap 128. As a result of the continued rotation of the cutting disc, the bone chips disposed against rib 143 slide over the cutting disc to a position in which the chips are pressed against the inner surface of the rib 145 that terminates over the inlet opening 152. As the chips rotate over outlet opening 96, the chips are presented with an additional opportunity to be forced through the openings 180 in the cutting disc and into the catch tray 220. One component of this force it is understood is the force imposed by the plunger 206 against the chips.

As a consequence of this chip-against-rib abutment, the chips may tumble on the cutting disc 172. Some chips may also tumble around ribs 143 and 145. The tumbling of the chips causes the chips to present different surfaces to the impingement plate 164 when they rotate against the plate. This can result in either the further shearing of the chips so they can fit through the openings 180 or the simple forcing of the chips through the openings 180 into the catch tray 220.

At the conclusion of the milling process, a fraction of the bone chips may remain adhered to the outer or top surface of the cutting disc 172. In part this may be due to the fact that fluid material integral with the bone chips causes the chips to adhere to the disc 172.

These chips can be harvested for use in the procedure for which the chips were milled. Specifically, to use these chips, the catch tray 220 is removed from the rest of the milling module 60. Plunger 206 is removed from the feed sleeve 156. To prevent the plunger 206 becoming a loose object in the operating room, the plunger is fitted between brackets 160. Specifically the plunger is press fit between the brackets so the short opposed sections of the brackets snap over the steps 210. The abutment of the end of the rod 207 distal from head 205 further prevents movement of the plunger when the plunger is releasably secured to the lid.

The milling module 60 is removed from the base module 32. This step is performed by actuating the linkage 46 so the linkage withdraws the tabs 44 from the rim 64 of mill head foundation 62. The lid 126 is removed from the foundation 62 of the mill milling module 60. Once this step is performed, milling element 170 can be removed so bone chips adhering to the milling element can be retrieved. The removal of the milling element 170 starts with the pushing up from the lower end of shaft 186. During a later sub-step of this process, shaft 186 functions as a handle that is used to hold the milling element 170. This reduces the extent to which the cutting disc 172 needs to be touched during this process. Once the milling element 170 is so extracted, using an appropriate tool, the bone chips adhering to cutting disc 172 are pushed into the catch tray 220. These bone chips, like the chips already in the catch tray 220, are thus available for use. That is, in a typical embodiment, the bone chips are discharged and collect in the catch tray 220. The catch tray is then removed from the milling module 60, and the bone chips are harvested for use.

A disadvantage of some bone mills is that sometimes the milled bone chips are not discharged from the mill housing. This is in part due to the nature of bone chips. These chips are moist. Therefore, there is a tendency of the chips to adhere to the surfaces of the mill head. In anticipation of this event occurring it has become a practice of some surgeons to harvest a volume of bone stock that is greater than the volume that is needed to be converted into bone chips. A surgeon will engage in this practice because the surgeon knows that a fraction of the bone stock will become trapped in the mill and not be discharged. Having to remove a volume of bone stock that is greater than the bone chips needed for the procedure serves to expose the patient to more trauma than to which he/she would otherwise be exposed if the surgeon was able to harvest a volume of bone stock that at the most is only marginally greater than the volume required to produce the necessary amount of bone chips. The features, e.g. accessible and removable milling element 170, of the milling module 60 described herein solve this disadvantage.

In one particular embodiment of the method, the milling element 170 includes the cutting disc 172 and the shaft 186, which is adapted to be held during removal of the milling element 170 from the foundation 62. The milling module 60 is removed from the base module 32. Then the milling element 170 from the foundation 62, the milling element 170 is removed via pushing up on a lower end of the shaft 186. The shaft 186 is then used as a handle for the milling element 170 thereby reducing the extent to which the cutting disc 172 needs to be touched. For example, the shaft 186 can be held an appropriate tool to push residual bone chips off the cutting disc 172 and into the catch tray 220. In one embodiment, the diameter of the cutting disc 172 and the opening on the catch tray correspond. As such, the cutting element 170 can be held via the shaft 186, and the cutting disc 172 can be inserted into the catch basin (e.g. diagonally) which is defined by its base 222, and the residual bone stock and/or bone chips can be harvested from the surface of the milling element 170, e.g. scraped of the surface of the cutting disc right into the catch basin.

In some embodiments of the method, the milling module 60 can be removed from the base module 32. In some such embodiments, the milling module 60 can be disposable and is thrown out. In other such embodiments, the milling module 60 is reusable and can be autoclaved. In yet other embodiments, the milling element 170 and/or catch tray 220 is disposable, and the milling module can be autoclaved and reused with a replacement milling element 170 and/or catch tray 220.

System 30 of this disclosure provides a means to use bone chips that while formed, would otherwise not be accessible for use. This feature can reduce the overall size of the bone stock the practitioner needs to harvest from the patient in order to supply the necessary volume of bone chips for the procedure. This is because the practitioner using this system knows that bone chips that remain on the cutting disc 172 after the milling process are retrievable for use. This means these bone chips do not have to be factored in as lost bone chips that, for a given volume of bone stock, reduce the volume of chips that are produced. This means the practitioner, knowing these otherwise lost chips will be retrieved, can reduce the volume of bone stock harvested from the patient in comparison to having to factor in that a fraction of the chips are lost. This reducing of the volume of the bone stock harvested serves to result in a like reduction in the trauma to which the patient is exposed as a result of the need to have to harvest the bone chips.

Another feature of this system is that sensor 54, controller 56, magnet 140 and rod 236 are configured to ensure that, the system will not run unless the lid 126 is properly secured to the foundation 62 and the catch tray 220 is properly seated in the foundation. This prevents operation of the system 30 in a situation where such operation can cause damage or physical harm.

It is a further benefit of this disclosure is that shaft 186 performs two functions. The shaft 186 serves as the transmission that supplies motive power from base module 32 to the cutting disc 172. The shaft 186 also serves as a handle during the process of retrieving the bone chips from the cutting disc 172.

The foregoing is directed to one specific version of the disclosure. Alternative versions of the disclosure may have different features from what has been described.

For example, there is no requirement all versions of the disclosure include the detection components and sensor system for determining whether or not the lid and catch tray are properly attached to the foundation. Similarly, some versions of this disclosure may not include a removable catch tray.

The features of the disclosure may likewise vary from what has been described. Thus, there is no requirement that in all versions of the disclosure the component of the milling component that converts the bone stock into bone chip be a disc. In some versions of the disclosure, this component may be a blade. Similarly, there is no requirement that, in all versions of the disclosure, the handle of the milling element be bi-functional. Thus, in some versions of the disclosure, the handle may only function as a handle for holding the milling component. Features other than the handle may function as the coupling features that transfer motive power to the milling component.

Likewise, in versions of the disclosure in which a sensor monitors whether or not the lid 126 and/or catch tray 220 are properly attached to the mill head may not always be a sensor that monitors the presence, absence of a magnetic field. In some versions of the disclosure. The sensor may be an optical sensor that emits a signal based on whether or not light at a particular wavelength is received. In these versions of the disclosure, the marker integral with the lid 126 may be a reflector. The detection component integral with the catch tray 220 may be an optic fiber of with a filter that allows light to pass through at the monitored wavelength. In other versions of the disclosure, the sensor may be mechanical switch. In these versions of the disclosure, the detection component may be static or moving mechanical components integral with the lid 126 and catch tray 220. As a result of these components going into registration or engaging, these components actuate the switch. The changing of the state of the signal across the switch is interpreted by the controller as indicating that the lid 126 and catch tray 220 are properly attached to the rest of the mill head.

In versions of the disclosure without a catch tray 220, a detection component may be associated with the foundation 62. This detection component could be a rod similar to rod 236. In this version of the disclosure only if the foundation 62 of the milling module 60 is properly attached to the base module 32 and the lid 126 is properly attached to the foundation 62 of the milling module 60 does the sensor output a signal indicating that these component are properly attached to the base module 32. Only when this signal is received does the controller 56 allow the motor 38 integral with the base module 32 to be actuated.

Further, while this disclosure is generally designed to convert bone stock into bone chips, this disclosure may have other uses. Using a different milling components the disclosure may be used to cut soft tissue into a form in which this tissue can be used in a procedure. Also, this disclosure may have applications other than in surgery.

The present disclosure also comprises the following clauses, with specific features laid out in dependent clauses, that may specifically be implemented as described in greater detail with reference to the configurations and drawings above.

I. A mill head 60 for converting bone stock into bone chips, said mill head comprising:
a shell 61 adapted for releasable attachment to base unit 32 that includes a motor 38, the base shell 34 having a first opening 152 through which bone stock is introduced into the shell 61 and second opening 96 through which bone chips are discharged from the shell 61;
a milling element 170, 186 moveably disposed in the shell 61 between the first opening 152 and the second opening 96 for converting bone stock into bone chips, the milling element including features 192 for removably attaching the milling element to the base unit motor 38 so that the actuation of the motor results in the actuation of the milling element,
Characterized in that:
the shell 61 consists of: a foundation 62 that is adapted for releasable attachment to the base unit 32, said base including the second opening 96 of the shell 61 and a lid 126 that is removably attached to said foundation 62, said lid including the first opening 152 of the shell 61, wherein, said base and said lid are collectively configured so that removal of the lid from the base allows the milling element 170 to be accessed; and
the milling element 170 is removably attached to said foundation 62 of said shell.

II. The mill head 60 for converting bone stock into bone chips of clause I further including:
a first indicia is mounted to said lid 126, said first indicia positioned to be detectable by a sensor 54 in the base unit 32 when the lid is correctly mounted to said shell 61; and
a second indicia 240 is mounted to said shell 61 and is positioned for detection by a sensor in the base unit, when the foundation 62 is attached to base unit 32.

III. The mill head 60 for converting bone stock into bone chips of clause II, wherein said first indicia is mounted to said lid 126 and said second indicia 240 is mounted to said shell 61 so that for said indicia to be detected by a single sensor 54 in the base unit 32, said first and second indicia must be in registration with each other and for said indicia to be in registration with each other, said lid 126 must be correctly secured to said base.

IV. The mill head 60 of clause II or III, wherein:
a catch tray 220 is removably mounted to said base 32 adjacent the second opening 96 to receive bone chips discharged to said second opening; and
said first indicia 240 of said base is attached to said catch tray 220 and positioned to only be in registration with said indicia of said lid 126 when said catch tray is correctly mounted to said base 32.

V. The mill head 60 of clause IV wherein:
said first indicia is a magnet 140; and
said second indicia is a component 236 formed from magnetically permeable material around which magnetic fields will develop.

VI. The mill head 60 of any one of clauses I to IV, wherein said milling element includes:
a cutting disk 172 with openings 174 and scallops 176 that convert bone stock into bone chips; and
a shaft 186 that extends from said cutting device that is adapted to be held during removal of the milling element from said foundation 62.

VII. The mill head 60 of clause VI, wherein said shaft 186 is a shaft that extends from said cutting device and is formed with the features 192 that removably couple the milling element 170 to the motor 38 of said base unit 32.

VIII. A method for operating a bone mill, the bone mill including a base module, a milling module 60, the milling module having a shell 61 adapted for releasable attachment to a base module 32 that includes a motor 38 and a sensor 54, the shell 61 including a lid, a foundation, and a catch try, said method comprising:
detecting whether the lid is coupled to the foundation, whether the catch tray is coupled to the foundation, and whether the milling module is coupled to the base module with a single sensor on the base module;
selectively powering the motor based on whether the lid is coupled to the foundation, the catch tray is coupled to the foundation, and whether the milling module is coupled to the base module.

IX. A method of converting bone stock into bone chips with a modular bone mill system 30 including a base module 32 and a milling module 60, the milling module 60 comprising a shell 61 adapted for releasable attachment to a base module 32, the shell 61 having: an inlet opening 152 through which bone stock is introduced into the shell 61, an outlet opening 96 through which bone chips are discharged from the shell 61 into a catch tray 220, and a milling element 170 moveably disposed in the shell 61 between the inlet opening 152 and the outlet opening 96 for converting bone stock into bone chips; and a foundation 62 that is adapted for releasable attachment to the base module 32, the foundation 62 including the outlet opening 96 of the shell 61, and a lid 126 that is removably attached to the foundation 62, the lid 126 including the inlet opening 152 of the shell 61, said method comprising the steps of:

introducing bone stock through the inlet opening 152 into the shell 61, actuating the milling element 170 to convert bone stock into bone chips and the discharge of bone chips through the outlet opening 96;

separating the first housing component from the second housing component subsequent to the actuation of the milling element 170 and the discharge of bone chips through said outlet opening 96; and harvesting residual bone chips from the surface of the milling element 170.

X. A modular bone processing system 30, the system comprising:

a base module 32 having a single detection sensor; and a bone processing module 60, said bone processing module comprising:

a shell 61 adapted for releasable attachment to a base module 32 that includes a motor 38 and a sensor 54, the shell 61 having:

a movable bone processing element, wherein the shell 61 includes:

a lid 126 that is removably attached to a foundation 62, the lid 126 including a first detection component 140 positioned to be detectable by the sensor 54 in the base module 32; and a foundation 62 being adapted for releasable attachment to the base module 32, the second housing member including a second detection component 236, wherein the first and second detection component 140, 236 are detectable by the single sensor 54 in the base module 32;

wherein the base module will not power the bone processing element of the bone processing module if the sensor 54 in the base module 32 does not detect the first and second detection components 140, 236.

XI. A milling module 60 comprising:

a shell 61 adapted for releasable attachment to a base module 32 that includes a motor 38 and a sensor 54, the shell 61 having:

an inlet opening 152 through which bone stock is introduced into the shell 61;

an outlet opening 96 through which bone chips are discharged from the shell 61; and a milling element 170 disposed in the shell 61 between the inlet opening 152 and the outlet opening 96 for converting bone stock into bone chips, wherein the shell 61 includes:

a lid 126 that is removably attached to a foundation 62, the lid 126 including the inlet opening 152 of the shell 61 and a first detection component 140 positioned to be detectable by the sensor 54 in the base module 32; and the foundation 62 being adapted for releasable attachment to the base module 32, the foundation 62 including the outlet opening 96 and a second detection component 236 and a catch tray 220 removably seated in the foundation 62 adjacent the outlet opening 96 to receive bone chips discharged therethrough, wherein the first and second detection component 140, 236 are detectable by the sensor 54 in the base module 32 when the lid 126 is attached to the foundation 62, the catch tray 220 is seated in the foundation 62, and the foundation 62 is attached to the base module 32.

XII. A milling module (60) for converting bone stock into bone chips, the milling module (60) comprising:

a shell (61) adapted for releasable attachment to a base module (32) that includes a motor (38), the shell (61) having:

an inlet opening (152) through which bone stock is introduced into the shell (61);

an outlet opening (96) through which bone chips are discharged from the shell (61); and a milling element (170) moveably disposed in the shell (61) between the inlet opening (152) and the outlet opening (96) for converting bone stock into bone chips, the milling element (170) includes a feature (192) for removably attaching the milling element (170) to the base module motor (38) so that the actuation of the motor (38) results in the actuation of the milling element (170), wherein the shell (61) includes a foundation (62) adapted for releasable attachment to the base module (32), the foundation (62) including the outlet opening (96) and a lid (126) that is removably attached to the foundation (62), the lid (126) including the inlet opening (152) of the shell (61), and wherein the foundation (62) and the lid (126) are collectively configured so that removal of the lid (126) from the foundation (62) allows the milling element (170) to be accessed.

XIII. The milling module (60) for converting bone stock into bone chips of clause XII, wherein the milling element (170) is removably attached to the foundation (62) of the shell (61).

XIV. The milling module (60) for converting bone stock into bone chips of clause XII or clause XIII further including:

a first detection component (140) mounted to the lid (126), the first detection component (140) positioned to be detectable by a sensor (54) in the base module (32) when the lid (126) is correctly mounted to the shell (61); and a second detection component (236) mounted to the foundation (62) and positioned for detection by the sensor (54) in the base module (32) when the foundation (62) is attached to the base module (32).

XV. The milling module (60) for converting bone stock into bone chips of clause XIV, wherein the first detection component (140) is mounted to the lid (126) and the second detection component (236) is mounted to the shell (61) so that for the first and second detection components (140, 236) are detectable by a single sensor (54) in the base module (32) when the first and second detection components (140, 236) are in registration with each other, and for the first detection component to be in registration for the second detection component, a catch tray (220) must be correctly seated in the foundation (62), and the foundation (62) must be correctly attached to the base module (32).

XVI. The milling module (60) of clause XIV or XV, wherein:

a catch tray (220) is removably mounted adjacent the outlet opening (96) to receive bone chips discharged therethrough; and the second detection component (236) of the foundation (62) is attached to the catch tray (220) and positioned to only be in registration with the first detection component (140) of the lid (126) when the catch tray (220) is correctly mounted to the foundation (62).

XVII. The milling module (60) of any one of clauses XIV to XVI, wherein:

the first detection component is a magnet (140); and the second detection component (236) is formed from magnetically permeable material around which magnetic fields will develop.

XVIII. The milling module (60) of any preceding clause, wherein the milling element (170) includes:

a cutting disc (172) with features (176) that convert bone stock into bone chips; and a shaft (186) that extends from the cutting disc (172), the shaft being adapted to be held during removal of the milling element (170) from the foundation (62).

XIX. The milling module (60) of clause XVIII, wherein the shaft (186) is operatively attached to a spring (187) and the shaft (186) and the spring (187) are configured such that when the lid (126) is not attached to the foundation (62), the shaft (186) will not attach to a drive spindle (40), the shaft (186) will not engage the cutting disc (172), or the shaft (186) will not operatively function, such that the cutting disc (172) cannot be actuated if the lid (126) is not correctly attached to the foundation (62).

XX. The milling module (60) of clause XIX, wherein the shaft (186) extends from the cutting disc (172) is formed with the features (192) that removably couple the milling element (170) to the motor (38) of the base module (32).

XXI. The milling module (60) of clause XX, wherein the shaft (186) includes a head (188) and a stem (190) that extends downwardly from the head (188), wherein the stem (190) includes one or more notches (192) that extend upwardly from a bottom face of the stem (190) and are spaced radially outwardly from the center of the stem (190), wherein the one or more notches (192) are configured to engage one or more complementary teeth on a face of the drive spindle (40) of the base module (32) so that the rotation of the drive spindle (40) results in the like rotation of the milling element (170).

XXII. The milling module (60) of clause XXI, wherein the cutting disc (172) includes one or more openings (174) which align with a complementary hole (175) on the head (188) of the shaft (186), wherein at least one pin (196) is positioned through one of said openings (174) and the complementary hole (175) such that the rotation of the shaft (186) results in the like rotation of the cutting disc (172).

XXIII The milling module (60) of clause XII, wherein the lid (126) includes a domed cap (128) which defines an inner surface (129) and a side wall (131).

XXIV. The milling module (60) of clause XXIII, wherein the cap (128) includes one or more tabs (130) that project radially outwardly from the side wall of the cap (128), wherein the one or more tabs (130) are positioned and dimensioned so that when the cap (128) is positioned in an opening (75) in the foundation (62) and rotated, each tab (130) rotates into a respective notch (106) in the foundation (62) to become integral with the notch (106) and correctly attach the lid (126) to the foundation (62).

XXV. The milling module (60) of clause XXIV, wherein one of the one or more tabs (130) includes a toe (138) having a first detection element (140) disposed therein and extending downwardly from one end of tab (130), wherein when cap (128) is positioned in the opening (75) in the foundation (62) and rotated to correctly attach the lid (126) to the foundation (62), the toe (138) moves into registration over an opening (112) in the foundation (62) when the lid (126) is correctly attached to the foundation (62).

XXVI. The milling module (60) of clause XXV, wherein the first detection element (140) is a magnet and a second detection element (234) is a rod (236) with high magnetic permeability in a sleeve (234), and a catch tray (220) includes a hollow sleeve (234) including the rod (236) therein, wherein the components forming the milling module (60) are formed so that when the lid (126) is correctly secured to the foundation (62) and the catch tray (220) is correctly seated in the foundation (62), the rod (236) is located below magnet (140).

XXVII. The milling module (60) as set forth in any one of clauses XXIII-XXVI, wherein the cap (128) includes one or more rings (142, 144, and 146) which extend downwardly from the inner surface (129) of the cap (128).

XXVIII. The milling module (60) of clause XXVII, wherein the cap (128) includes an outermost ring (146) which is positioned on an outer perimeter of the cap (128), wherein the outermost ring (146) of the lid (126) seats against a step (88) on the foundation (62) when fitted thereto.

XXIX. The milling module (60) in any one of clauses XXIII-XXVIII, wherein the cap (128) includes one or more ribs (143, 145) extending downwardly from the inner surface (129) of the cap (128), the ribs (143, 145) configured to push bone stock into a cutting disc (172) of the milling element (170) and prevent bone stock from accumulating on the inner surface (129) of the cap (128) when the milling module (60) is in operation.

XXX. The milling module (60) of clause XXIX, wherein at least one rib (145) extends inwardly from an intermediate ring (144) and angles away from the location on the intermediate ring (144) from which the rib (143) extends, but does not extend to an innermost ring (142), wherein the at least one rib (145) curves in the direction of rotation of the cutting disc (172).

XXXI. The milling module (60) of clause XXIX or XXX, wherein at least one rib (145) extends inwardly from the innermost ring (142) and angles away from the location on the innermost ring (142) from which the rib (143) extends, but does not extend to the intermediate ring (144), wherein the at least one rib (143) curves in the direction of rotation of the cutting disc (172).

XXXII. The milling module (60) as set forth in any preceding clause, wherein the foundation (62) includes a rim (64) having plural openings (66) and is dimensioned to seat around an outer perimeter of a top surface (36) of the base module (32), wherein when seated plural tabs (44) on the base module (32) extend through the plural openings (66) to become integral with the plural openings (66) and correctly attach the milling module (60) to the base module (32).

XXXIII A modular bone mill system (30) for converting bone stock into bone chips, the system comprising:

a base module (32); and a milling module (60), said milling module comprising:

a shell (61) adapted for releasable attachment to a base module (32) that includes a motor (38) and a sensor (54), the shell (61) having:

an inlet opening (152) through which bone stock is introduced into the shell (61);

an outlet opening (96) through which bone chips are discharged from the shell (61); and a milling element (170) disposed in the shell (61) between the inlet opening (152) and the outlet opening (96) for converting bone stock into bone chips, wherein the shell (61) includes:
a lid (126) that is removably attached to a foundation (62), the lid (126) including the inlet opening (152) of the shell (61) and a first detection component (140) positioned to be detectable by the sensor (54) in the base module (32); and
the foundation (62) being adapted for releasable attachment to the base module (32), the foundation (62) including the outlet opening (96) and a second detection component (236) and a catch tray (220) removably seated in the foundation (62) adjacent the outlet opening (96) to receive bone chips discharged therethrough, wherein the base module is configured to selectively power the milling element (170) of the milling module (60) based on whether the sensor (54) in the base module (32) detects that the first and second detection components (140, 236) are arranged relative to each other indicating that the lid (126) is correctly attached to the foundation (62), the catch tray (220) is correctly seated in the foundation (62), and the foundation (62) is correctly attached to the base module (32).

XXXIV. The modular bone mill system (30) of clause XXXIII, wherein the first detection component (140) is mounted to the lid (126) and the second detection component (236) is mounted to the foundation, the base module including a single sensor for determining that the first and said second detection components (140, 236) are in registration with each other, which is indicative that the lid (126) is correctly secured to the foundation (62), the catch tray (220) is correctly seated in the foundation (62), and the foundation (62) is correctly attached to the base module (32).

XXXV. The modular bone mill system (30) of clause XXXIII or XXXIV, wherein the second detection component (236) of the foundation (62) is attached to the catch tray (220) and positioned to only be in registration with the first detection component (140) of the lid (126) when the catch tray (220) is correctly mounted to the foundation (62).

XXXVI. The modular bone mill system (30) of any one of clauses XXXIII-XXXV, wherein:
the first detection component is a magnet (140); and
the second detection component (236) is formed from magnetically permeable material around which magnetic fields will develop.

XXXVII. The modular bone mill system (30) of any one of clauses XXXIII-XXXVI, wherein the milling element (170) includes:
a cutting disc (172) with features (176) that convert bone stock into bone chips; and
a shaft (186) that extends from the cutting disc (172) that is adapted to be held during removal of the milling element (170) from the foundation (62).

XXXVIII. The modular bone mill system (30) of clause XXXVII, wherein the shaft (186) extends from the cutting disc (172) and is formed with features (192) that removably couple the milling element (170) to the motor (38) of the base module (32).

XXXIX. The modular bone mill system (30) of clause XXXVIII, wherein the shaft (186) includes a head (188) and a stem (190) that extends downwardly from the head (188), wherein the stem (190) includes one or more notches (192) that extend upwardly from a bottom face of the stem (190) and are spaced radially outwardly from the center of the stem (190), wherein the one or more notches (192) are configured to engage one or more complementary teeth on a face of a drive spindle (40) of the base module (32) so that rotation of the drive spindle (40) results in like rotation of the milling element (170).

XL. The modular bone mill system (30) of clause XXXIX, wherein the cutting disc (172) includes one or more openings (174) which align with a complementary hole (175) on the head (188) of the shaft (186), wherein at least one pin (196) is positioned through one of said openings (174) and the complementary hole (175) such that the rotation of the shaft (186) results in the like rotation of the cutting disc (172).

XLI. The modular bone mill system (30) as set forth in any one of clauses XXXIII-XL, wherein the milling element (170) is removably attached to the foundation (62) of the shell (61).

XLII. The modular bone mill system (30) of any one of clauses XXXIII-XLI, wherein the lid (126) includes a domed, disc shaped cap (128) which defines an inner surface (129) and a side wall (131).

XLIII. The modular bone mill system (30) of clause XLII, wherein the cap (128) includes one or more tabs (130) that project radially outwardly from a cylindrical side wall of the cap, wherein the one or more tabs (130) are positioned and dimensioned so that when cap (128) is positioned in an opening (75) in the foundation (62) and rotated, each tab (130) rotates into a respective notch (106) in the foundation (62) to become integral with the notch (106) and correctly attach the lid (126) to the foundation (62).

XLIV. The modular bone mill system (30) of clause XLIII, wherein one of the one or more tabs (130) includes a toe (138) having a magnet (140) disposed therein and extending downwardly from one end of tab (130), wherein when the cap (128) is positioned in an opening (75) in the foundation (62) and rotated to correctly attach the lid (126) to the foundation (62), the toe (138) moves into registration over an opening (112) in the foundation (62) when the lid (126) is correctly attached to the foundation (62).

XLV. The modular bone mill system (30) of clause XLIV, wherein the catch tray (220) includes a hollow sleeve (234) including a rod (236) with high magnetic permeability in the sleeve (234), wherein the components forming the milling module (60) are formed so that when the lid (126) is correctly secured to the foundation (62) and the catch tray (220) is correctly seated in the foundation (62), the rod (236) is located below the magnet (140).

XLVI. The modular bone mill system (30) as set forth in any one of clauses XLII-XLV, wherein the cap (128) includes one or more rings (142, 144, and 146) which extend downwardly from the inner surface (129) of the cap (128).

XLVII. The modular bone mill system (30) of clause XLVI, wherein the cap (128) includes an outermost ring (146) which is positioned on an outer perimeter of the cap (128), wherein the outermost ring (146) of the lid (126) seats against a step (88) on the foundation (62) when fitted thereto.

XLVIII. The modular bone mill system (30) in any of clauses XLII-XLVII, wherein the cap (128) includes one or more ribs (143, 145) extending downwardly from the inner surface (129) of the cap (128), the ribs (143, 145) configured to push bone stock into a cutting disc (172) of the milling element (170) and prevent bone stock from accumulating on the inner surface (129) of the cap (128) when the bone mill is in operation.

XLIX. The modular bone mill system (30) of clause XLVIII, wherein at least one rib (143) extends inwardly from an intermediate ring (144) and angles away from a location on the intermediate ring (144) from which the rib (145) extends, but does not extend to an innermost ring (142), wherein the at least one rib (145) curves in the direction of rotation of the cutting disc (172).

L. The modular bone mill system of (30) of clause XLVIII or XLIX, wherein at least one rib (145) extends inwardly from the innermost ring (142) and angles away from the location on the innermost ring (142) from which the rib (143) extends, but does not extend to the intermediate ring (144), wherein the at least one rib (143) curves in the direction of rotation of the cutting disc (172).

LI. The modular bone mill system (30) of any one of clauses XXXIII-L, wherein the foundation (62) includes a rim (64) having plural openings (66) and is dimensioned to seat around an outer perimeter of a top surface (36) of the base module (32), wherein when the milling module (60) is seated over the base module (32) top surface (36), plural tabs (44) on the base module (32) extend through the plural openings (66) to become integral with the plural opening (66) and correctly attach the milling module (60) to the base module (32).

LII. A method of converting bone stock into bone chips with a modular bone mill system (30) including a base module (32) and a milling module (60), the milling module (60) comprising a shell (61) adapted for releasable attachment to a base module (32), the shell (61) having an inlet opening (152) through which bone stock is introduced into the shell (61), an outlet opening (96) through which bone chips are discharged from the shell (61) into a catch tray (220), and a milling element (170) moveably disposed in the shell (61) between the inlet opening (152) and the outlet opening (96) for converting bone stock into bone chips, a foundation (62) that is adapted for releasable attachment to the base module (32), the foundation (62) including the outlet opening (96) of the shell (61), and a lid (126) that is removably attached to the foundation (62), the lid (126) including the inlet opening (152) of the shell (61), said method comprising the steps of:
 introducing bone stock through the inlet opening (152) into the shell (61),
 actuating the milling element (170) to convert bone stock into bone chips and the discharge of bone chips through the outlet opening (96);
 opening the lid (126) subsequent to the actuation of the milling element (170) and the discharge of bone chips through said outlet opening (96); and
 harvesting residual bone chips from the surface of the milling element (170).

LIII. The method of converting bone stock into bone chips as set forth in clause LII, further comprising the step of removing the milling element (170) from the foundation (62) to access any residual bone chips from a surface of the milling element (170).

LIV. The method of converting bone stock into bone chips as set forth in clause LII or LIII, further comprising the step of removing the catch tray (220) and harvesting the discharged bone chips from the catch tray.

LV. The method of converting bone stock into bone chips as set forth in any one of clauses LII-LIV, further comprising the step of attaching the milling module (60) to the base module (32).

LVI. The method of converting bone stock into bone chips as set forth in any one of clauses LII-LV, further comprising the step of releasing the milling module (60) from the base module (32).

LVII. The method of converting bone stock into bone chips as set forth in clause LVI, further comprising the step of disposing of the milling module (60).

LVIII. The method of converting bone stock into bone chips as set forth in any one of clauses LII-LVII, further comprising the step of attaching the lid (126) to the foundation (62) and mounting the catch tray (220) on the base module (32) adjacent the outlet opening (96) to receive bone chips discharged through the outlet opening (96).

LIX. The method of converting bone stock into bone chips as set forth in any one of clauses LII-LVIII, wherein the milling element (170) includes a cutting disc (172) and a shaft (186) that is adapted to be held during removal of the milling element (170) from the foundation (62) and wherein the step of removing the milling element (170) from the foundation (62) is further defined as removing the milling element (170) via pushing up on a lower end of the shaft (186).

LX. The method of converting bone stock into bone chips as set forth in clause LIX, further comprising the step of using the shaft (186) as a handle for the milling element (170) thereby reducing the extent to which the cutting disc (172) needs to be touched.

LXI. The method of converting bone stock into bone chips as set forth in clause LX, further comprising the step of using a tool to remove residual bone stock and/or bone chips off the cutting disc (172) and into the catch tray (220).

LXII. The method of converting bone stock into bone chips as set forth in clause LX, further comprising the step of inserting the cutting disc (172) at least partially into the catch tray (220) and scraping residual bone stock and/or bone chips into the catch tray (220).

LXIII. A milling module (60) for converting bone stock into bone chips, the milling module (60) comprising:
 a shell (61) adapted for releasable attachment to a base module (32) that includes a motor (38) and a drive spindle (40), the shell (61) having:
  an inlet opening (152) through which bone stock is introduced into the shell (61);
  an outlet opening (96) through which bone chips are discharged from the shell (61); and
  a milling element (170) moveably disposed in the shell (61) between the inlet opening (152) and the outlet opening (96) for converting bone stock into bone chips, the milling element (170) including:
   a cutting disc (172) with features (176) that convert bone stock into bone chips; and
   a shaft (186) and a spring (187) that extends from the cutting disc (172), said shaft (186) having a feature (192) for removably attaching the milling element (170) to the drive spindle (40) so that actuation of the motor (38) results in actuation of the milling element (170),
  a foundation (62) adapted for releasable attachment to the base module (32), the foundation (62) including the outlet opening (96) and a lid (126) that is removably attached to the foundation (62), the lid (126) including the inlet opening (152) of the shell (61), and
 wherein the foundation (62) and the lid (126) are collectively configured so that removal of the lid (126) from the foundation (62) allows the milling element (170) to be accessed; and wherein the shaft (186) and the spring (187) are collectively configured so that when the lid (126) is not attached to the foundation (62): the shaft (186) will not attach to the drive spindle (40); the shaft (186) will not engage the cutting disc (172); or the shaft (186) will not operatively function, such that the cutting disc (172) cannot be actuated if the lid (126) is not correctly attached to the foundation (62).

Accordingly, it is an object of the appended claims to cover all such variations and modifications that come within the true spirit and scope of this disclosure.

What is claimed is:

1. A modular bone mill system for converting bone stock into bone chips, the system comprising:
   a base module including a motor and a sensor; and
   a milling module, the milling module comprising:
      a shell adapted for releasable attachment to the base module, the shell having:
         an inlet opening through which bone stock is introduced into the shell;
         an outlet opening through which bone chips are discharged from the shell; and
         a milling element disposed in the shell between the inlet opening and the outlet opening for converting bone stock into bone chips; and
      a lid that is removably attached to a foundation, the lid including the inlet opening of the shell and a first detection component positioned to be detectable by the sensor in the base module, and the foundation being adapted for releasable attachment to the base module, the foundation including the outlet opening and a second detection component and a catch tray removably seated in the foundation adjacent the outlet opening to receive bone chips discharged therethrough;
   wherein the base module is configured to selectively power the milling element of the milling module based on whether the sensor in the base module detects that the first and second detection components are arranged relative to each other indicating that the lid is correctly attached to the foundation, the catch tray is correctly seated in the foundation, and the foundation is correctly attached to the base module;
   wherein the lid includes a domed, disc shaped cap which defines an inner surface and a side wall;
   wherein the cap includes one or more tabs that project radially outwardly from a cylindrical side wall of the cap, with the one or more tabs positioned and dimensioned so that when cap is positioned in an opening in the foundation and rotated, each tab rotates into a respective notch in the foundation to become integral with the notch and correctly attach the lid to the foundation; and
   wherein one of the one or more tabs includes a toe having a magnet disposed therein and extending downwardly from one end of tab, wherein when the cap is positioned in an opening in the foundation and rotated to correctly attach the lid to the foundation, the toe moves into registration over an opening in the foundation when the lid is correctly attached to the foundation.

2. The modular bone mill system of claim 1, wherein the first detection component is mounted to the lid and the second detection component is mounted to the foundation, the base module including a single sensor for determining that the first and the second detection components are in registration with each other, which is indicative that the lid is correctly secured to the foundation, the catch tray is correctly seated in the foundation, and the foundation is correctly attached to the base module.

3. The modular bone mill system of claim 1, wherein the second detection component of the foundation is attached to the catch tray and positioned to only be in registration with the first detection component of the lid when the catch tray is correctly mounted to the foundation.

4. The modular bone mill system of claim 1, wherein: the first detection component is a magnet, and the second detection component is formed from magnetically permeable material around which magnetic fields will develop.

5. The modular bone mill system of claim 1, wherein the milling element includes: a cutting disc with features that convert bone stock into bone chips; and a shaft that extends from the cutting disc that is adapted to be held during removal of the milling element from the foundation.

6. The modular bone mill system of claim 5, wherein the shaft extends from the cutting disc and is formed with features that removably couple the milling element to the motor of the base module.

7. The modular bone mill system of claim 6, wherein the shaft includes a head and a stem that extends downwardly from the head, wherein the stem includes one or more notches that extend upwardly from a bottom face of the stem and are spaced radially outwardly from the center of the stem, wherein the one or more notches are configured to engage one or more complementary teeth on a face of a drive spindle of the base module so that rotation of the drive spindle results in like rotation of the milling element.

8. The modular bone mill system of claim 7, wherein the cutting disc includes one or more openings which align with a complementary hole on the head of the shaft, wherein at least one pin is positioned through one of the openings and a corresponding hole such that rotation of the shaft results in like rotation of the cutting disc.

9. The modular bone mill system of claim 1, wherein the milling element is removably attached to the foundation of the shell.

10. The modular bone mill system of claim 1, wherein the catch tray includes a hollow sleeve including a rod with magnetic permeability in the sleeve, wherein the components forming the milling module are formed so that when the lid is correctly secured to the foundation and the catch tray is correctly seated in the foundation, the rod is located below the magnet.

11. A modular bone mill system for converting bone stock into bone chips, the system comprising:
   a base module including a motor and a sensor; and
   a milling module, the milling module comprising:
      a shell adapted for releasable attachment to the base module, the shell having:
         an inlet opening through which bone stock is introduced into the shell;
         an outlet opening through which bone chips are discharged from the shell; and
         a milling element disposed in the shell between the inlet opening and the outlet opening for converting bone stock into bone chips; and
      a lid that is removably attached to a foundation, the lid including the inlet opening of the shell and a first detection component positioned to be detectable by the sensor in the base module, and the foundation being adapted for releasable attachment to the base module, the foundation including the outlet opening and a second detection component and a catch tray removably seated in the foundation adjacent the outlet opening to receive bone chips discharged therethrough;

wherein the base module is configured to selectively power the milling element of the milling module based on whether the sensor in the base module detects that the first and second detection components are arranged relative to each other indicating that the lid is correctly attached to the foundation, the catch tray is correctly seated in the foundation, and the foundation is correctly attached to the base module; and wherein the lid includes a domed, disc shaped cap which defines an inner surface and a side wall and the cap includes one or more rings which extend downwardly from the inner surface of the cap.

12. The modular bone mill system of claim 11, wherein the cap includes an outermost ring which is positioned on an outer perimeter of the cap, wherein the outermost ring of the lid seats against a step on the foundation when fitted thereto.

13. A modular bone mill system for converting bone stock into bone chips, the system comprising:
a base module including a motor and a sensor; and
a milling module, the milling module comprising:
a shell adapted for releasable attachment to the base module, the shell having:
an inlet opening through which bone stock is introduced into the shell;
an outlet opening through which bone chips are discharged from the shell; and
a milling element disposed in the shell between the inlet opening and the outlet opening for converting bone stock into bone chips; and
a lid that is removably attached to a foundation, the lid including the inlet opening of the shell and a first detection component positioned to be detectable by the sensor in the base module, and the foundation being adapted for releasable attachment to the base module, the foundation including the outlet opening and a second detection component and a catch tray removably seated in the foundation adjacent the outlet opening to receive bone chips discharged therethrough;

wherein the base module is configured to selectively power the milling element of the milling module based on whether the sensor in the base module detects that the first and second detection components are arranged relative to each other indicating that the lid is correctly attached to the foundation, the catch tray is correctly seated in the foundation, and the foundation is correctly attached to the base module; and wherein the lid includes a domed, disc shaped cap which defines an inner surface and a side wall and the cap includes one or more ribs extending downwardly from the inner surface of the cap, the ribs configured to push bone stock into a cutting disc of the milling element and prevent bone stock from accumulating on the inner surface of the cap when the bone mill is in operation.

14. The modular bone mill system of claim 13, wherein at least one rib extends inwardly from an intermediate ring and angles away from a location on the intermediate ring from which the rib extends, but does not extend to an innermost ring, wherein the at least one rib curves in the direction of rotation of the cutting disc.

15. The modular bone mill system of claim 14, wherein at least one rib extends inwardly from the innermost ring and angles away from the location on the innermost ring from which the rib extends, but does not extend to the intermediate ring, wherein the at least one rib curves in the direction of rotation of the cutting disc.

* * * * *